United States Patent
McCue et al.

(10) Patent No.: US 7,375,259 B1
(45) Date of Patent: May 20, 2008

(54) SOLANUM TUBEROSUM STEROL ALKALOID GLYCOSYLTRANSFERASE (SGT) A NOVEL SOLANIDINE GLUCOSYLTRANSFERASE SGT2 AND USES THEREOF

(75) Inventors: Kent F. McCue, El Cerrito, CA (US); Paul V. Allen, Pinole, CA (US); David R. Rockhold, El Cerrito, CA (US); Louise V. T. Shepherd, Errol (GB); Mary M. Maccree, Woodland, CA (US); Howard V. Davies, Invergowire (GB); William R. Belknap, Albany, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 108 days.

(21) Appl. No.: 11/272,952

(22) Filed: Nov. 14, 2005

(51) Int. Cl.
*A01H 1/00* (2006.01)
*C07H 21/04* (2006.01)
*C12N 15/29* (2006.01)
*C12N 15/52* (2006.01)
*C07K 14/415* (2006.01)

(52) U.S. Cl. .................... 800/295; 435/6; 435/69.1; 435/468; 435/419; 435/252.3; 435/320.1; 435/183; 530/370; 536/23.6; 800/278

(58) Field of Classification Search ................ 435/6, 435/69.1, 468, 419, 252.3, 320.1, 183; 530/370; 536/23.6; 800/278, 296
See application file for complete search history.

(56) References Cited

U.S. PATENT DOCUMENTS 5,959,180 A 9/1999 Moehs et al.

FOREIGN PATENT DOCUMENTS

WO WO 2004078979 A1 * 9/2004

OTHER PUBLICATIONS

Bergenstrahle, A., E. Tillberg, and L. Jonsson, "Characterization of UDP-glucose:solanidine glucosyltransferase and UDP-galactose:solanidine galactosyltransferase from potato tuber," Plant Science (1992) 84:35-44.
Draper, J., and R. Scott, Chapter 4 "The Isolation of plant nucleic acid," In: Plant Genetic Transformation and Gene Expression—A Laboratory Manual, Eds: J. Draper, R. Scott, P. Armitage and R. Walden, (1998) Blackwell Scientific Publications pp. 199-236.
Esposito, F. et al., "Glycoalkaloid Content and Chemical Composition of Potatoes Improved with Nonconventional Breeding Approaches," J. Agric. Food Chem. (2002) 50:1553-1561.
McCue, K., et al., "The Primary in vivo steroidal alkaloid glucosyltransferase from potato," Phytochemistry (2006) In press.
McCue, K. et al., "Reduction of Total Steroidal Glycoalkaloids in Potato Tubers Using Antisense Constructs of a Gene Encoding a Solanidine Glucosyl Transferase," Acta Hort. (2003) 619:77-86.
McCue, K. et al., "Metobalic compensation of steroidal glycoalkaloid biosynthesis in transgenic potato tubers: using reverse genetics to confirm the in vivo enzyme function of a steroidal alkaloid galactosyltransferase," Plant Science (2005) 168:267-273.
Mensinga, T.T., et al., "Potato glycoalkaloids and adverse effects in humans: an ascending dose study," Regulatory Toxicology and Pharmacology (2005) 41:66-72.
Moehs, C.P., P. Allen, M. Friedman, and W.R. Belknap, "Cloning and expression of solanidine UDP-glucose glucosyltransferase from potato," The Plant Journal (1997) 11(2):227-236.
Paczkowski, C. and Z.A. Wojciechowski, "Glucosylation and Galactosylation of Diosgenin and Solasodine by Soluble Glycosyltransferase(s) from *Solanum melongena* Leaves," Phytochemistry (1994) 35(6):1429-1434.
Stapleton, A., P.A. Allen, M. Friedman, and W.R. Belknap, "Purification and Characterization of Solanidine Glucosyltransferase from the Potato (*Solanum tuberosum*)," J. Agric. Food Chem. (1991) 39:1187-1193.
Valkonen, J.P.T., M. Keskitalo, T. Vasara and L. Pietila, "Potato Glycoalkaloids: A Burden or A Blessing?" Critical Reviews in Plant Sciences (1996) 15(1):1-20.
Van Der Leij, F.R., R.G.F. Visser, A.S. Ponstein, E. Jacobsen, and W.J. Feenstra, "Sequence of the structural gene for granule-bound starch synthase of potato (*Solanum tuberosum* L.) and evidence for a single point deletion in the amf allel," Mol. Gen. Genet. (1991) 228:240-248.
Zimowski, J., "Occurence of a Glucosyltransferase Specific for Solanidine in Potato Plants," Phytochemistry (1991) 30(6):1827-1831.

* cited by examiner

*Primary Examiner*—Phuong Bui
(74) *Attorney, Agent, or Firm*—Elizabeth R. Sampson; Margaret A. Connor; Leslie Shaw

(57) ABSTRACT

Nucleic acid sequences from potato that encode the enzyme UDP-glucose:solanidine glucosyltransferase (SGT2) are disclosed. Recombinant DNA molecules containing the sequences, and use thereof, in particular, use of the sequences and antisense constructs to inhibit the production of SGT2 and thereby reduce the level of the more human-toxic of the two predominant steroidal glycoalkaloids α-chaconine and/or increase the level of the more insect-toxic α-solanine in Solanaceous plants such as potato are described.

11 Claims, 13 Drawing Sheets

```
SOLtu_Sgt2.1   ------------------------------------ATGGATAACGGGAGCAAGCAAC  22
SOLtu_Sgt1     GAAACAACAACTGTTCTTGGGTAGTAAAAATGGTAGCAACCTGCAACAATGGCGAAATCC  60
                                                   *   *** ** *     *

SOLtu_Sgt2.1   TACATGTCCTCTTCCTTCCTTACTTCGCCACTGGTCATATCATTCCATTAGTTAACGCTG  82
SOLtu_Sgt1     TCCATGTTCTTTTCCTTCCCTTCTTATCCGCTGGTCATTTCATCCCATTAGTTAACGCCG  120
               * ***** **  ******** ***  ** ******** *** ************** *

SOLtu_Sgt2.1   CCAGGCTATTCGCCTCCCGTGACGGTGTCAAAGTTACCATCCTCACTACCCACCACAATG  142
SOLtu_Sgt1     CAAGGCTATTCGCCTCCCG---CGGTGTTAAAGCCACAATCCTCACTACCCCTCATAATG  177
               * ****************    ****** ****  ** ************    ** ****

SOLtu_Sgt2.1   CTTCCCTCTTCCGATCTTCTATTGACAAT------------------TCCCTAATCTCTA  184
SOLtu_Sgt1     CCTTACTTTTTAGATCTACTATTGACGATGATGTTCGAATTTCCGGATTTCCCATTTCTA  237
               * *  ** ** ***** ********* **                  *   *  ** ****

SOLtu_Sgt2.1   TCGTTACTCTTAAGTTCCCTTCCACTGAAGTTGGGTTGCCTGAAGGGATCGAAAATTTCA  244
SOLtu_Sgt1     TCGTAACTATTAAATTCCCCTCTGCTGAAGTTGGGTTGCCTGAAGGAATTGAGAGCTTTA  297
               **** *** **** *****   * *********************  **  * * ** *

SOLtu_Sgt2.1   GCTCCGCCTCTTCAACTGAAATCGCGGGCAAAGTATTTGGCGGCACATATCTTCTGCAGA  304
SOLtu_Sgt1     ACTCTGCCACTTCACCTGAAATGCCTCATAAAATTTTTTATGCTCTTTCTCTTCTACAAA  357
                *** *** ****  ******* *    *** ** * ***      *  * ****** *

SOLtu_Sgt2.1   AACCAATGGAAGATAAAATTCGTGAAATCCATCCTGATTGTATCTTCTCTGATATGTATT  364
SOLtu_Sgt1     AGCCAATGGAAGATAAAATTCGTGAACTCCGTCCTGATTGCATTTTTTCTGATATGTACT  417
               * ************************ *** ********  ** ** ***********  *

SOLtu_Sgt2.1   TCCCATGGACTGTCGATATTGCCCTGGAGCTCAAAATCCCCAGGCTATTGTTCAACCAAT  424
SOLtu_Sgt1     TCCCTTGGACAGTAGATATTGCTGATGAGCTTCACATCCCTCGTATTTTGTACAATTTGT  477
               **** ***** ** ******** *   ****  ** ***** *  ***  ** *** *  *

SOLtu_Sgt2.1   CTAGCTACATGTACAATTCCATTCTGTATAATCTTAGGCTTTACAAACCTCATGAAAAAC  484
SOLtu_Sgt1     CTGCTTACATGTGCTACAGCATTATGCACAACCTTAAGGTTTACAGACCTCACAAGCAGC  537
               **  ******* *  *   *** **  *  ** **** * ***** *****  *   * *

SOLtu_Sgt2.1   TCATCAATCAGATGGAATATTCCAAAAGTACTAATTTCTCGGTTCCGGATTTACCTGATA  544
SOLtu_Sgt1     CTA--ATCTAGACGAA---TCTCAAA-------GTTCGTGGTTCCTGGTTTACCTGATG  585
                *   *** * *  **    * ***         ****  ****** * **********

SOLtu_Sgt2.1   AGATCGAGTTCAAGCTATCGCAACTTACAGACGATCTGGTAAGGCCTGCGGATGAGAGGA  604
SOLtu_Sgt1     AGATAAAGTTCAAGTTATCCCAACTGACAGATGATCTGAGAAAGTCGGATGACCAAAAGA  645
               ****  ******** **** ***** ***** ******  * *    *  ****  * **

SOLtu_Sgt2.1   ATGCTTTTGATGAATTGCTCGATCGAACCAGAGAATCTGAGGATCTAAGCTACGGAATCG  664
SOLtu_Sgt1     CTGTTTTTGACGAATTGCTCGAACAAGTTGAAGATTCGGAGGAACGAAGCTATGGCATTG  705
                ** ****** ***********  * *    ** **  **** * * ***** **  * *

SOLtu_Sgt2.1   TTCATGATACTTTTTACGAGCTAGAACCTGCCTACGCTGACTACTATCAGAAGATGAAGA  724
SOLtu_Sgt1     TTCATGATACATTTTATGAGCTAGAACCTGCATATGTTGACTACTACCAGAAATTAAAGA  765
               ********** ***** ************** ** * ********* ***** * ****
```

FIG. 2A

```
SOLtu_Sgt2.1    AAACCAAATGTTGGCAAATTGGTCCCATTTCCTATTTTTCTTCCAAATTATCCCCAAGAA 784
SOLtu_Sgt1      AACCAAAATGTTGGCATTTTGGTCCGCTCTCTCATTTTGCATCCAAAAT---CCGTAGTA 822
                ** * ********** ******* * **  ***** * ******  *    ** ** *

SOLtu_Sgt2.1    AAGAACTGATTAATTCTTCTGATGAAAGTAACTCATCTGCCGTTGTTGTAGAGTGGTTGA 844
SOLtu_Sgt1      AGGAACTAATT------TCTGAGCATAACAAC---AATGAGATTGTTATAGATTGGTTGA 873
                * ***** ***      ****  * *  ***    **  ***** *** *** ******

SOLtu_Sgt2.1    ATAAACATAAGCACAAATCGGTCCTCTACGTCTCTTTTGGGAGCACAATTAGATTCCCAG 904
SOLtu_Sgt1      ATGCACAGAAACCTAAATCGGTTCTCTATGTATCTTTCGGAAGCATGGCTAGATTTCCTG 933
                **  ***  ** * ******* ***** ** ***** *** ****    ****** ** *

SOLtu_Sgt2.1    AGGAGCAACTCGCTGAAATCGCAAAAGCTCTAGAAGCTTCTACCGTCCCTTTCATTTGGG 964
SOLtu_Sgt1      AGAGCCAACTGAATGAAATAGCCCAAGCTCTGGATGCTTCAAATGTTCCTTTCATTTTTG 993
                ** *  *****   ****** **  ******* **  ****** * ** ********** *

SOLtu_Sgt2.1    TAGTAAACAAAGACCAATTAGCAAAAACCACGTGGTTACCGGAGAGTTTGTTCGATGAGA 1024
SOLtu_Sgt1      TATTGAGGCCTAATGAAGAAACGGCGTCGTGGTTGCCAGTTGGTAATTTAGAGGACAAGA 1053
                ** *     *    *     *  **    * *  * ** * *  *    *** ** ***

SOLtu_Sgt2.1    ---AAAAATGTCTGATTATTAAAGGGTGGGCACCGCAACTATCCATCTTAGATCATTCAG 1081
SOLtu_Sgt1      CTAAAAAGGGTTTGTACATCAAAGGGTGGGTCCCACAGCTTACGATCATGGAACATTCAG 1113
                   ****   **  ** **  ********* ** ** **  ** *  ** ** ******

SOLtu_Sgt2.1    CAGTCGGAGGATTCATGACACACTGTGGTTGGAATTCAGTGCTTGAAGCCATCATCGCCG 1141
SOLtu_Sgt1      CAACAGGCGGGTTCATGACTCATTGTGGTACTAATTCGGTTCTGGAAGCCATCACTTTTG 1173
                **   **  ** ******** **  *****    *****  **  *********      *

SOLtu_Sgt2.1    GGGTGCCGTTGGTGACGTGGCCAGTGTTCGCTGAACAATTCTACAATGAAAAACTAGTGG 1201
SOLtu_Sgt1      GCGTGCCAATGATAACATGGCCACTTTATGCTGATCAATTCTACAACGAGAAGGTAGTCG 1233
                * *****  **  ** ****** *  *  *****  ********** ** **  ****  *

SOLtu_Sgt2.1    AGGTTATGGGCTAGGAGTGAAAGTAGGGGCAGAAGTATATAACACCAACGGAGGTGCTG 1261
SOLtu_Sgt1      AGGTTAGGGGATTGGGAATCAAAATCGGGATAGATGTATGGAA------TGAAGGGATTG 1287
                ****** ***  * ***  * *** * ***  ***  *** *  **      *   ** **

SOLtu_Sgt2.1    AGATATCGACCCCTGTGTTAAGGAGCGAAAAGATAAAAGAAGCAATTGAGAGGTTAATG- 1320
SOLtu_Sgt1      AGATCACGGGCCCTGTAATAGAAAGCGCCAAGATTAGAGAAGCAATTGAGAGACTAATGA 1347
                ****  ** ****** **   ****   *****  *  ***************  *****

SCLtu_Sgt2.1    ---------------GAAAGTCAGAAA-ATAAGAGAGAAAGCAGTGAGTATGAGTAAGA 1363
SCLtu_Sgt1      TCAGTAATGGTTCTGAGGAAATTATAAATATTAGGGATAGAGTAATGGCTATGAGCAAAA 1407
                                * ** * *** ** ** **  * ** * ** ****** ** *

SOLtu_Sgt2.1    TGGCTAAAAATGCAGTGGAAGAAGGTGGATCTTCATCGAACAATCTTACCGCACTTATAG 1423
SOLtu_Sgt1      TGGCTCAGAATGCAACAAATGAAGGTGGATCTTCGTGGAACAATCTCACTGCTCTCATTC 1467
                ***** * ******    **  ************  * ******** ** ** ** **

SOLtu_Sgt2.1    ATGATATCAAGAATTTTACTTCTTCTTCATTGAAGATCATGGATTAACAACTTAAAGTTT 1483
SOLtu_Sgt1      AACATATCAAGAATTATAATCTTAATTAGTTGGAAGACAGAAATAAGT--CCTTGCATTG 1525
                *  *********** **   * ** * * ***  *** *  **  **    ***   **
```

FIG. 2B

```
SOLtu_Sgt2.1    CGACTAGGGCTGGGAATAAACACCGAGAAATCGAAACACCAAATCTAATTGAATTATTTT 1543
SOLtu_Sgt1      TAACTTGGTGTGTGTGTGTGTTTTTTTTCCACTTAATAAAATGAAGGAATGGATGGATG- 1584
                ***  **  **  *  *                *  **  *       *  ** **    *

SOLtu_Sgt2.1    GATTTCGATATTTCGATATTCGATATATATTTTCGTATTTTTTGGTATTTCGATTCAAGT 1603
SOLtu_Sgt1      GATCTTAACTTTAAAAAAAAAAAAAAAAAA------------------------------ 1614
                *** *   *  **   *  *     *  *  *

SOLtu_Sgt2.1    TTCGGTATGTAATTTTATATTATTCGATATTTCAGTTTACCAAAAAAAAAAAAAAA 1659
SOLtu_Sgt1      -------------------------------------------------------
```

FIG. 2C

```
SGT1    1      MVATCNSGEILHVLFLPFLSAGHFIPLVNAARLFASR-GVKATILTTPHNALLFRSTIDD
SGT2    1      ---MDNGSKQLHVLFLPYFATGHIIPLVNAARLFASRDGVKVTILTTHHNASLFRSSIDN
               *..: ******:::**:************** ***.***** *** ****:**:

SGT1    60     DVRISGFPISIVTIKFPSAEVGLPEGIESFNSATSPEMPHKIFYALSLLQKPMEDKIREL
SGT2    58     SL------ISIVTLKFPSTEVGLPEGIENFSSASSTEIAGKVFGGTYLLQKPMEDKIREI
               .:      *****:****:*********.*.**:*.*:. *:*  . ************:

SGT1    120    RPDCIFSDMYFPWTVDIADELHIPRILYNLSAYMCYSIMHNLKVYRPHK----QPNLDES
SGT2    112    HPDCIFSDMYFPWTVDIALELKIPRLLFNQSSYMYNSILYNLRLYKPHEKLINQMEYSKS
               :***************** **:***:::* *:**  **::**::*:**:    *  ..:*

SGT1    176    QSFVVPGLPDEIKFKLSQLTDDLRKSDDQKTVFDELLEQVEDSEERSYGIVHDTFYELEP
SGT2    172    TNFSVPDLPDKIEFKLSQLTDDLVRPADERNAFDELLDRTRESEDLSYGIVHDTFYELEP
               .* **.***:*:********** :. *::..****:: ..:**: **************

SGT1    236    AYVDYYQKLKKPKCWHFGPLSHFASKIRS-KELIS---EHNNNEIVIDWLNAQKPKSVLY
SGT2    232    AYADYYQKMKKTKCWQIGPISYFSSKLSPRKELINSSDESNSSAVVVEWLNKHKHKSVLY
               **.*****:**.***: **:*:*:**:.  ****.   * *..  :*:**  :* *****

SGT1    292    VSFGSMARFPESQLNEIAQALDASNVPFIFVLRPNEETAS-WLPVGNLEDKTKKGLYIKG
SGT2    292    VSFGSTIRFPEEQLAEIAKALEASTVPPIWVVNKDQLAKTTWLPES-LFDE-KKCLIIKG
               ***** ****:.** ***:**:**.** *:*: :: :  : ***  *  *: ** * ***

SGT1    351    WVPQLTIMEHSATGGFMTHCGTNSVLEAITFGVPMITWPLYADQFYNEKVVEVRGLGIKI
SGT2    350    WAPQLSILDHSAVGGFMTHCGWNSVLEAIIAGVPLVTWPVFAEQFYNEKLVEVMGLGVKV
               *.***:*::***.******** ******  .***::***::*:*****:*** ***:*:

SGT1    411    GIDVWN--EGIEITGPVIESAKIREAIERLMISNGSEEIINIRDRVMAMSKMAQNATNEG
SGT2    410    GAEVYNTNGGAEISTPVLRSEKIKEAIERLMESQ------KIREKAVSMSKMAKNAVEEG
               * :*:*    * **: **:.* **:****** *:      :**:. :.:*****:**.**

SGT1    469    GSSWNNLTALIQHIKNYNLN------
SGT2    464    GSSSNNLTALIDDIKNFTSSSLKIMD
               ***.*******:..***: ..     .
```

FIG. 3

SEQUENCE LISTING

<160> NUMBER OF SEQ ID NOS: 21

<210> SEQ ID NO 1
<211> LENGTH: 1659
<212> TYPE: DNA
<213> ORGANISM: Solanum tuberosum Sgt2.1
<220> FEATURE:
<221> NAME/KEY: CDS
<222> LOCATION: (1)..(1470)

<400> SEQUENCE: 1

```
atg gat aac ggg agc aag caa cta cat gtc ctc ttc ctt cct tac ttc      48
Met Asp Asn Gly Ser Lys Gln Leu His Val Leu Phe Leu Pro Tyr Phe
1               5                  10                  15 gcc act ggt cat atc att cca tta gtt aac gct gcc agg cta ttc gcc      96
Ala Thr Gly His Ile Ile Pro Leu Val Asn Ala Ala Arg Leu Phe Ala
                20                  25                  30 tcc cgt gac ggt gtc aaa gtt acc atc ctc act acc cac cac aat gct     144
Ser Arg Asp Gly Val Lys Val Thr Ile Leu Thr Thr His His Asn Ala
            35                  40                  45 tcc ctc ttc cga tct tct att gac aat tcc cta atc tct atc gtt act     192
Ser Leu Phe Arg Ser Ser Ile Asp Asn Ser Leu Ile Ser Ile Val Thr
        50                  55                  60 ctt aag ttc cct tcc act gaa gtt ggg ttg cct gaa ggg atc gaa aat     240
Leu Lys Phe Pro Ser Thr Glu Val Gly Leu Pro Glu Gly Ile Glu Asn
65                  70                  75                  80 ttc agc tcc gcc tct tca act gaa atc gcg ggc aaa gta ttt ggc ggc     288
Phe Ser Ser Ala Ser Ser Thr Glu Ile Ala Gly Lys Val Phe Gly Gly
                85                  90                  95 aca tat ctt ctg cag aaa cca atg gaa gat aaa att cgt gaa atc cat     336
Thr Tyr Leu Leu Gln Lys Pro Met Glu Asp Lys Ile Arg Glu Ile His
                100                 105                 110 cct gat tgt atc ttc tct gat atg tat ttc cca tgg act gtc gat att     384
Pro Asp Cys Ile Phe Ser Asp Met Tyr Phe Pro Trp Thr Val Asp Ile
            115                 120                 125 gcc ctg gag ctc aaa atc ccc agg cta ttg ttc aac caa tct agc tac     432
Ala Leu Glu Leu Lys Ile Pro Arg Leu Leu Phe Asn Gln Ser Ser Tyr
        130                 135                 140 atg tac aat tcc att ctg tat aat ctt agg ctt tac aaa cct cat gaa     480
Met Tyr Asn Ser Ile Leu Tyr Asn Leu Arg Leu Tyr Lys Pro His Glu
145                 150                 155                 160 aaa ctc atc aat cag atg gaa tat tcc aaa agt act aat ttc tcg gtt     528
Lys Leu Ile Asn Gln Met Glu Tyr Ser Lys Ser Thr Asn Phe Ser Val
                165                 170                 175 ccg gat tta cct gat aag atc gag ttc aag cta tcg caa ctt aca gac     576
Pro Asp Leu Pro Asp Lys Ile Glu Phe Lys Leu Ser Gln Leu Thr Asp
                180                 185                 190 gat ctg gta agg cct gcg gat gag agg aat gct ttt gat gaa ttg ctc     624
Asp Leu Val Arg Pro Ala Asp Glu Arg Asn Ala Phe Asp Glu Leu Leu
            195                 200                 205 gat cga acc aga gaa tct gag gat cta agc tac gga atc gtt cat gat     672
Asp Arg Thr Arg Glu Ser Glu Asp Leu Ser Tyr Gly Ile Val His Asp
        210                 215                 220
```

```
act ttt tac gag cta gaa cct gcc tac gct gac tac tat cag aag atg      720
Thr Phe Tyr Glu Leu Glu Pro Ala Tyr Ala Asp Tyr Tyr Gln Lys Met
225                 230                 235                 240 aag aaa acc aaa tgt tgg caa att ggt ccc att tcc tat ttt tct tcc      768
Lys Lys Thr Lys Cys Trp Gln Ile Gly Pro Ile Ser Tyr Phe Ser Ser
                245                 250                 255 aaa tta tcc cca aga aaa gaa ctg att aat tct tct gat gaa agt aac      816
Lys Leu Ser Pro Arg Lys Glu Leu Ile Asn Ser Ser Asp Glu Ser Asn
        260                 265                 270 tca tct gcc gtt gtt gta gag tgg ttg aat aaa cat aag cac aaa tcg      864
Ser Ser Ala Val Val Val Glu Trp Leu Asn Lys His Lys His Lys Ser
    275                 280                 285 gtc ctc tac gtc tct ttt ggg agc aca att aga ttc cca gag gag caa      912
Val Leu Tyr Val Ser Phe Gly Ser Thr Ile Arg Phe Pro Glu Glu Gln
290                 295                 300 ctc gct gaa atc gca aaa gct cta gaa gct tct acc gtc cct ttc att      960
Leu Ala Glu Ile Ala Lys Ala Leu Glu Ala Ser Thr Val Pro Phe Ile
305                 310                 315                 320 tgg gta gta aac aaa gac caa tta gca aaa acc acg tgg tta ccg gag     1008
Trp Val Val Asn Lys Asp Gln Leu Ala Lys Thr Thr Trp Leu Pro Glu
                325                 330                 335 agt ttg ttc gat gag aaa aaa tgt ctg att att aaa ggg tgg gca ccg     1056
Ser Leu Phe Asp Glu Lys Lys Cys Leu Ile Ile Lys Gly Trp Ala Pro
                340                 345                 350 caa cta tcc atc tta gat cat tca gca gtc gga gga ttc atg aca cac     1104
Gln Leu Ser Ile Leu Asp His Ser Ala Val Gly Gly Phe Met Thr His
        355                 360                 365 tgt ggt tgg aat tca gtg ctt gaa gcc atc atc gcc ggg gtg ccg ttg     1152
Cys Gly Trp Asn Ser Val Leu Glu Ala Ile Ile Ala Gly Val Pro Leu
    370                 375                 380 gtg acg tgg cca gtg ttc gct gaa caa ttc tac aat gaa aaa cta gtg     1200
Val Thr Trp Pro Val Phe Ala Glu Gln Phe Tyr Asn Glu Lys Leu Val
385                 390                 395                 400 gag gtt atg ggg cta gga gtg aaa gta ggg gca gaa gta tat aac acc     1248
Glu Val Met Gly Leu Gly Val Lys Val Gly Ala Glu Val Tyr Asn Thr
                405                 410                 415 aac gga ggt gct gag ata tcg acc cct gtg tta agg agc gaa aag ata     1296
Asn Gly Gly Ala Glu Ile Ser Thr Pro Val Leu Arg Ser Glu Lys Ile
                420                 425                 430 aaa gaa gca att gag agg tta atg gaa agt cag aaa ata aga gag aaa     1344
Lys Glu Ala Ile Glu Arg Leu Met Glu Ser Gln Lys Ile Arg Glu Lys
        435                 440                 445 gca gtg agt atg agt aag atg gct aaa aat gca gtg gaa gaa ggt gga     1392
Ala Val Ser Met Ser Lys Met Ala Lys Asn Ala Val Glu Glu Gly Gly
    450                 455                 460 tct tca tcg aac aat ctt acc gca ctt ata gat gat atc aag aat ttt     1440
Ser Ser Ser Asn Asn Leu Thr Ala Leu Ile Asp Asp Ile Lys Asn Phe
465                 470                 475                 480 act tct tct tca ttg aag atc atg gat taa caacttaaag tttcgactag       1490
Thr Ser Ser Ser Leu Lys Ile Met Asp
                485 ggctgggaat aaacaccgag aaatcgaaac accaaatcta attgaattat tttgatttcg   1550 atatttcgat attcgatata tattttcgta tttttggta tttcgattca agtttcggta    1610 tgtaatttta tattattcga tatttcagtt taccaaaaaa aaaaaaaaa               1659

<210> SEQ ID NO 2
<211> LENGTH: 489
<212> TYPE: PRT
```

<213> ORGANISM: Solanum tuberosum Sgt2.1

<400> SEQUENCE: 2

```
Met Asp Asn Gly Ser Lys Gln Leu His Val Leu Phe Leu Pro Tyr Phe
1               5                   10                  15

Ala Thr Gly His Ile Ile Pro Leu Val Asn Ala Ala Arg Leu Phe Ala
            20                  25                  30

Ser Arg Asp Gly Val Lys Val Thr Ile Leu Thr Thr His His Asn Ala
        35                  40                  45

Ser Leu Phe Arg Ser Ser Ile Asp Asn Ser Leu Ile Ser Ile Val Thr
    50                  55                  60

Leu Lys Phe Pro Ser Thr Glu Val Gly Leu Pro Glu Gly Ile Glu Asn
65                  70                  75                  80

Phe Ser Ser Ala Ser Ser Thr Glu Ile Ala Gly Lys Val Phe Gly Gly
                85                  90                  95

Thr Tyr Leu Leu Gln Lys Pro Met Glu Asp Lys Ile Arg Glu Ile His
            100                 105                 110

Pro Asp Cys Ile Phe Ser Asp Met Tyr Phe Pro Trp Thr Val Asp Ile
        115                 120                 125

Ala Leu Glu Leu Lys Ile Pro Arg Leu Leu Phe Asn Gln Ser Ser Tyr
    130                 135                 140

Met Tyr Asn Ser Ile Leu Tyr Asn Leu Arg Leu Tyr Lys Pro His Glu
145                 150                 155                 160

Lys Leu Ile Asn Gln Met Glu Tyr Ser Lys Ser Thr Asn Phe Ser Val
                165                 170                 175

Pro Asp Leu Pro Asp Lys Ile Glu Phe Lys Leu Ser Gln Leu Thr Asp
            180                 185                 190

Asp Leu Val Arg Pro Ala Asp Glu Arg Asn Ala Phe Asp Glu Leu Leu
        195                 200                 205

Asp Arg Thr Arg Glu Ser Glu Asp Leu Ser Tyr Gly Ile Val His Asp
    210                 215                 220

Thr Phe Tyr Glu Leu Glu Pro Ala Tyr Ala Asp Tyr Tyr Gln Lys Met
225                 230                 235                 240

Lys Lys Thr Lys Cys Trp Gln Ile Gly Pro Ile Ser Tyr Phe Ser Ser
                245                 250                 255

Lys Leu Ser Pro Arg Lys Glu Leu Ile Asn Ser Ser Asp Glu Ser Asn
            260                 265                 270

Ser Ser Ala Val Val Glu Trp Leu Asn Lys His Lys His Lys Ser
        275                 280                 285

Val Leu Tyr Val Ser Phe Gly Ser Thr Ile Arg Phe Pro Glu Glu Gln
    290                 295                 300

Leu Ala Glu Ile Ala Lys Ala Leu Glu Ala Ser Thr Val Pro Phe Ile
305                 310                 315                 320

Trp Val Val Asn Lys Asp Gln Leu Ala Lys Thr Thr Trp Leu Pro Glu
                325                 330                 335

Ser Leu Phe Asp Glu Lys Lys Cys Leu Ile Ile Lys Gly Trp Ala Pro
            340                 345                 350

Gln Leu Ser Ile Leu Asp His Ser Ala Val Gly Gly Phe Met Thr His
        355                 360                 365

Cys Gly Trp Asn Ser Val Leu Glu Ala Ile Ile Ala Gly Val Pro Leu
    370                 375                 380

Val Thr Trp Pro Val Phe Ala Glu Gln Phe Tyr Asn Glu Lys Leu Val
385                 390                 395                 400
```

```
Glu Val Met Gly Leu Gly Val Lys Val Gly Ala Glu Val Tyr Asn Thr
            405                 410                 415

Asn Gly Gly Ala Glu Ile Ser Thr Pro Val Leu Arg Ser Glu Lys Ile
        420                 425                 430

Lys Glu Ala Ile Glu Arg Leu Met Glu Ser Gln Lys Ile Arg Glu Lys
            435                 440                 445

Ala Val Ser Met Ser Lys Met Ala Lys Asn Ala Val Glu Glu Gly Gly
        450                 455                 460

Ser Ser Ser Asn Asn Leu Thr Ala Leu Ile Asp Asp Ile Lys Asn Phe
465                 470                 475                 480

Thr Ser Ser Ser Leu Lys Ile Met Asp
                485

<210> SEQ ID NO 3
<211> LENGTH: 1449
<212> TYPE: DNA
<213> ORGANISM: Solanum tuberosum Sgt 2.2
<220> FEATURE:
<221> NAME/KEY: CDS
<222> LOCATION: (1)..(1449)

<400> SEQUENCE: 3
```

| | | | | | | | | | | | | | | | | |
|---|---|---|---|---|---|---|---|---|---|---|---|---|---|---|---|---|
| atg | gat | aac | ggg | agc | aag | caa | cta | cac | gtc | ctc | ttc | ctt | cct | tac | ttc | 48 |
| Met | Asp | Asn | Gly | Ser | Lys | Gln | Leu | His | Val | Leu | Phe | Leu | Pro | Tyr | Phe | |
| 1 | | | | 5 | | | | | 10 | | | | | 15 | | |
| gcc | act | ggt | cat | atc | att | cca | tta | gtt | aac | gct | gcc | agg | cta | ttc | gcc | 96 |
| Ala | Thr | Gly | His | Ile | Ile | Pro | Leu | Val | Asn | Ala | Ala | Arg | Leu | Phe | Ala | |
| | | | 20 | | | | | 25 | | | | | 30 | | | |
| tcc | cgt | ggc | ggt | gtc | aaa | gtt | acc | att | ctc | act | acc | cac | cac | aat | gct | 144 |
| Ser | Arg | Gly | Gly | Val | Lys | Val | Thr | Ile | Leu | Thr | Thr | His | His | Asn | Ala | |
| | | 35 | | | | | 40 | | | | | 45 | | | | |
| tcc | ctc | ttc | cga | tct | tct | att | gac | aat | tcc | cta | atc | tct | atc | gct | act | 192 |
| Ser | Leu | Phe | Arg | Ser | Ser | Ile | Asp | Asn | Ser | Leu | Ile | Ser | Ile | Ala | Thr | |
| | 50 | | | | | 55 | | | | | 60 | | | | | |
| ctt | aag | ttc | cct | tcc | act | gaa | gtt | ggg | ttg | cct | gaa | ggg | atc | gaa | aat | 240 |
| Leu | Lys | Phe | Pro | Ser | Thr | Glu | Val | Gly | Leu | Pro | Glu | Gly | Ile | Glu | Asn | |
| 65 | | | | | 70 | | | | | 75 | | | | | 80 | |
| ttc | agc | tcc | gcc | tct | tca | act | gaa | atc | gcg | agc | aaa | tta | ttt | ggc | ggc | 288 |
| Phe | Ser | Ser | Ala | Ser | Ser | Thr | Glu | Ile | Ala | Ser | Lys | Leu | Phe | Gly | Gly | |
| | | | | 85 | | | | | 90 | | | | | 95 | | |
| att | tat | ctt | ctg | cag | aaa | cca | atg | gaa | gat | aaa | att | cgt | gaa | atc | cat | 336 |
| Ile | Tyr | Leu | Leu | Gln | Lys | Pro | Met | Glu | Asp | Lys | Ile | Arg | Glu | Ile | His | |
| | | | | 100 | | | | | 105 | | | | | 110 | | |
| cct | gat | tgt | atc | ttc | tct | gat | atg | tat | ttc | cca | tgg | act | gtc | gat | att | 384 |
| Pro | Asp | Cys | Ile | Phe | Ser | Asp | Met | Tyr | Phe | Pro | Trp | Thr | Val | Asp | Ile | |
| | | | 115 | | | | | 120 | | | | | 125 | | | |
| gca | ctg | gag | ctc | aaa | atc | ccc | agg | cta | ttg | ttc | aac | caa | tct | agc | tac | 432 |
| Ala | Leu | Glu | Leu | Lys | Ile | Pro | Arg | Leu | Leu | Phe | Asn | Gln | Ser | Ser | Tyr | |
| | | 130 | | | | | 135 | | | | | 140 | | | | |
| atg | tac | aat | tcc | att | ctg | tac | aat | ctt | agg | ctt | tac | aaa | cct | cac | gaa | 480 |
| Met | Tyr | Asn | Ser | Ile | Leu | Tyr | Asn | Leu | Arg | Leu | Tyr | Lys | Pro | His | Glu | |
| 145 | | | | | 150 | | | | | 155 | | | | | 160 | |
| tat | tcc | aaa | agt | agt | aat | ttc | tcg | gtt | ccg | ggt | tta | cct | gat | aag | atc | 528 |
| Tyr | Ser | Lys | Ser | Ser | Asn | Phe | Ser | Val | Pro | Gly | Leu | Pro | Asp | Lys | Ile | |
| | | | | 165 | | | | | 170 | | | | | 175 | | |
| gag | ttc | aat | cta | tcg | caa | ctt | aca | gac | gat | ctg | ata | aag | cct | gca | gat | 576 |
| Glu | Phe | Asn | Leu | Ser | Gln | Leu | Thr | Asp | Asp | Leu | Ile | Lys | Pro | Ala | Asp | |
| | | | | 180 | | | | | 185 | | | | | 190 | | |
| gag | agg | aat | ggt | ttt | gat | gaa | ttg | ctc | gat | cga | acc | aga | gaa | tct | gag | 624 |
| Glu | Arg | Asn | Gly | Phe | Asp | Glu | Leu | Leu | Asp | Arg | Thr | Arg | Glu | Ser | Glu | |

-continued

```
                195                 200                 205
gat caa agc tac ggt atc gtt cat gat act ttt tac gaa cta gaa cct      672
Asp Gln Ser Tyr Gly Ile Val His Asp Thr Phe Tyr Glu Leu Glu Pro
210                 215                 220 gcc tac gct gac tac tat cag aag atg aag aaa acc aaa tgt tgg caa      720
Ala Tyr Ala Asp Tyr Tyr Gln Lys Met Lys Lys Thr Lys Cys Trp Gln
225                 230                 235                 240 att ggt ccc att tcc tat ttt tct tcc aaa tta ttc cga aga aaa gat      768
Ile Gly Pro Ile Ser Tyr Phe Ser Ser Lys Leu Phe Arg Arg Lys Asp
                245                 250                 255 ctg att aat tct ttt gat gaa agt aac tca tct gcc gct gtt gta gag      816
Leu Ile Asn Ser Phe Asp Glu Ser Asn Ser Ser Ala Ala Val Val Glu
            260                 265                 270 tgg ttg aat aaa cag aag cac aaa tcg gtc ctc tac gtc tct ttc ggg      864
Trp Leu Asn Lys Gln Lys His Lys Ser Val Leu Tyr Val Ser Phe Gly
        275                 280                 285 agc aca gtt aaa ttc cca gag gag caa ctc gct gaa atc gca aaa gct      912
Ser Thr Val Lys Phe Pro Glu Glu Gln Leu Ala Glu Ile Ala Lys Ala
    290                 295                 300 cta gaa gct tct acc gtc cct ttc att tgg gta gtg aag gag gac caa      960
Leu Glu Ala Ser Thr Val Pro Phe Ile Trp Val Val Lys Glu Asp Gln
305                 310                 315                 320 tca gca aaa acc acc tgg tta ccg gag agt ttg ttc gat gag aaa aaa     1008
Ser Ala Lys Thr Thr Trp Leu Pro Glu Ser Leu Phe Asp Glu Lys Lys
                325                 330                 335 ggt ctg att att aaa ggg tgg gct ccg caa cta acc atc tta gat cat     1056
Gly Leu Ile Ile Lys Gly Trp Ala Pro Gln Leu Thr Ile Leu Asp His
            340                 345                 350 tca gca gta gga gga ttc atg aca cac tgt gga tgg aat tcg gtg ctt     1104
Ser Ala Val Gly Gly Phe Met Thr His Cys Gly Trp Asn Ser Val Leu
        355                 360                 365 gaa gct atc atc gct ggg gtg ccg ttg gtg acg tgg cca gtg ttc gct     1152
Glu Ala Ile Ile Ala Gly Val Pro Leu Val Thr Trp Pro Val Phe Ala
    370                 375                 380 gaa caa ttc tac aat gaa aaa ctt gtg gag gtt atg gag cta gga gtg     1200
Glu Gln Phe Tyr Asn Glu Lys Leu Val Glu Val Met Glu Leu Gly Val
385                 390                 395                 400 aaa gta ggg gca gaa gta cat aac tcc gac gga tgt gtt gag ata tcg     1248
Lys Val Gly Ala Glu Val His Asn Ser Asp Gly Cys Val Glu Ile Ser
                405                 410                 415 agc cct gtg tta agg agc gaa aag ata aaa gaa gca att gag agg tta     1296
Ser Pro Val Leu Arg Ser Glu Lys Ile Lys Glu Ala Ile Glu Arg Leu
            420                 425                 430 atg gaa agt cag aaa ata aga gag aaa gca gtg agt atg agt aag atg     1344
Met Glu Ser Gln Lys Ile Arg Glu Lys Ala Val Ser Met Ser Lys Met
        435                 440                 445 gct aaa aat gca gtg gaa gaa ggt gga tct tca tgg aac aat ctt acc     1392
Ala Lys Asn Ala Val Glu Glu Gly Gly Ser Ser Trp Asn Asn Leu Thr
    450                 455                 460 gca ctt ata gat gat atc aag aat ttt act tct tct tca ttg aag atc     1440
Ala Leu Ile Asp Asp Ile Lys Asn Phe Thr Ser Ser Ser Leu Lys Ile
465                 470                 475                 480 atg gat taa                                                          1449
Met Asp <210> SEQ ID NO 4
<211> LENGTH: 482
<212> TYPE: PRT
<213> ORGANISM: Solanum tuberosum Sgt 2.2
```

```
<400> SEQUENCE: 4

Met Asp Asn Gly Ser Lys Gln Leu His Val Leu Phe Leu Pro Tyr Phe
1               5                   10                  15

Ala Thr Gly His Ile Ile Pro Leu Val Asn Ala Ala Arg Leu Phe Ala
            20                  25                  30

Ser Arg Gly Gly Val Lys Val Thr Ile Leu Thr Thr His His Asn Ala
            35                  40                  45

Ser Leu Phe Arg Ser Ser Ile Asp Asn Ser Leu Ile Ser Ile Ala Thr
50                  55                  60

Leu Lys Phe Pro Ser Thr Glu Val Gly Leu Pro Glu Gly Ile Glu Asn
65                  70                  75                  80

Phe Ser Ser Ala Ser Ser Thr Glu Ile Ala Ser Lys Leu Phe Gly Gly
                85                  90                  95

Ile Tyr Leu Leu Gln Lys Pro Met Glu Asp Lys Ile Arg Glu Ile His
                100                 105                 110

Pro Asp Cys Ile Phe Ser Asp Met Tyr Phe Pro Trp Thr Val Asp Ile
            115                 120                 125

Ala Leu Glu Leu Lys Ile Pro Arg Leu Leu Phe Asn Gln Ser Ser Tyr
130                 135                 140

Met Tyr Asn Ser Ile Leu Tyr Asn Leu Arg Leu Tyr Lys Pro His Glu
145                 150                 155                 160

Tyr Ser Lys Ser Ser Asn Phe Ser Val Pro Gly Leu Pro Asp Lys Ile
                165                 170                 175

Glu Phe Asn Leu Ser Gln Leu Thr Asp Asp Leu Ile Lys Pro Ala Asp
                180                 185                 190

Glu Arg Asn Gly Phe Asp Glu Leu Leu Asp Arg Thr Arg Glu Ser Glu
                195                 200                 205

Asp Gln Ser Tyr Gly Ile Val His Asp Thr Phe Tyr Glu Leu Glu Pro
            210                 215                 220

Ala Tyr Ala Asp Tyr Gln Lys Met Lys Lys Thr Lys Cys Trp Gln
225                 230                 235                 240

Ile Gly Pro Ile Ser Tyr Phe Ser Ser Lys Leu Phe Arg Arg Lys Asp
                245                 250                 255

Leu Ile Asn Ser Phe Asp Glu Ser Asn Ser Ser Ala Ala Val Val Glu
                260                 265                 270

Trp Leu Asn Lys Gln Lys His Lys Ser Val Leu Tyr Val Ser Phe Gly
            275                 280                 285

Ser Thr Val Lys Phe Pro Glu Glu Gln Leu Ala Glu Ile Ala Lys Ala
            290                 295                 300

Leu Glu Ala Ser Thr Val Pro Phe Ile Trp Val Val Lys Glu Asp Gln
305                 310                 315                 320

Ser Ala Lys Thr Thr Trp Leu Pro Glu Ser Leu Phe Asp Glu Lys Lys
                325                 330                 335

Gly Leu Ile Ile Lys Gly Trp Ala Pro Gln Leu Thr Ile Leu Asp His
                340                 345                 350

Ser Ala Val Gly Gly Phe Met Thr His Cys Gly Trp Asn Ser Val Leu
            355                 360                 365

Glu Ala Ile Ile Ala Gly Val Pro Leu Val Thr Trp Pro Val Phe Ala
370                 375                 380

Glu Gln Phe Tyr Asn Glu Lys Leu Val Glu Val Met Glu Leu Gly Val
385                 390                 395                 400

Lys Val Gly Ala Glu Val His Asn Ser Asp Gly Cys Val Glu Ile Ser
                405                 410                 415
```

```
Ser Pro Val Leu Arg Ser Glu Lys Ile Lys Glu Ala Ile Glu Arg Leu
        420                 425                 430

Met Glu Ser Gln Lys Ile Arg Glu Lys Ala Val Ser Met Ser Lys Met
        435                 440                 445

Ala Lys Asn Ala Val Glu Glu Gly Gly Ser Ser Trp Asn Asn Leu Thr
    450                 455                 460

Ala Leu Ile Asp Asp Ile Lys Asn Phe Thr Ser Ser Ser Leu Lys Ile
465                 470                 475                 480

Met Asp

<210> SEQ ID NO 5
<211> LENGTH: 1011
<212> TYPE: DNA
<213> ORGANISM: Solanum tuberosum Sgt2.1 partial Sequence

<400> SEQUENCE: 5
atctgcagaa ttcggcttga tggttagttg cggtgcccac cctttaataa tcagacattt      60
tttctcatcg aacaaactct ccggtaacca cgtggttttt gctaattggt ctttgtttac     120
tacccaaatg aaagggacgg tagaagcttc tagagctttt gcgatttcag cgagttgctc     180
ctctgggaat ctaattgtgc tcccaaaaga gacgtagagg accgatttgt gcttatgttt     240
attcaaccac cctacaacaa cggcagatga gttactttca tcagaagaat taatcagttc     300
ttttcttggg gataatttgg aagaaaaata ggaaatggga ccaatttgcc aacatttggt     360
tttcttcatc ttctgatagt agtcagcgta ggcaggttca agctcgtaaa agtatcatg     420 aacgattccg tagcttagat cctcagattc tctggttcga tcgagcaatt catcaaaagc     480
attccyctca tccgcaggcc ttaccagatc gtctgtaagt tgcgatagct tgaacccgat     540
cttatcaggt aaatccggaa ccgagaaatt agtactttg gaatattcca tctgattgat      600 gagttttca tgaggtttgt aaagcctaag attatacaga atggaattgt acatgtagct     660
agattggttg aacaatagcc tggggatttt gagctccagg gcaatatcga cagtccatgg     720
gaaatacata tcagagaaga tacaatcagg atggatttca cgaattttat cttccattgg     780
tttctgcaga agatatgtgc cgccaaatac tttgcccgcg atttcagttg aagaggcgga     840
gctgaaattt tcgatcccctt caggcaaccc aacttcagtg aagggaact taagagtaac     900 gatagagatt agggaattgt caatagaaga tcggaagagg aagcattgt ggtgggtagt      960 gaggatggta actttgacac cgtcacggga ggcgaatagc ctggcagcgt t            1011

<210> SEQ ID NO 6
<211> LENGTH: 19
<212> TYPE: DNA
<213> ORGANISM: Artificial
<220> FEATURE:
<223> OTHER INFORMATION: Primer WRB 1384 - Forward

<400> SEQUENCE: 6
cttccttcct tacttcgcc                                                   19

<210> SEQ ID NO 7
<211> LENGTH: 17
<212> TYPE: DNA
<213> ORGANISM: Artificial
<220> FEATURE:
<223> OTHER INFORMATION: Primer WRB 1386 - Forward

<400> SEQUENCE: 7
```

```
ggataacggg agcaagc                                                   17

<210> SEQ ID NO 8
<211> LENGTH: 18
<212> TYPE: DNA
<213> ORGANISM: Artificial
<220> FEATURE:
<223> OTHER INFORMATION: Primer WRB 1414 - Reverse

<400> SEQUENCE: 8
gatggttagt tgcggtgc                                                  18

<210> SEQ ID NO 9
<211> LENGTH: 19
<212> TYPE: DNA
<213> ORGANISM: Artificial
<220> FEATURE:
<223> OTHER INFORMATION: Primer WRB 1453 Sgt2 3-prime Forward

<400> SEQUENCE: 9
taccgtccct ttcatttgg                                                 19

<210> SEQ ID NO 10
<211> LENGTH: 20
<212> TYPE: DNA
<213> ORGANISM: Artificial
<220> FEATURE:
<223> OTHER INFORMATION: Primer WRB 1526 PCR gt11 Rev - M13 Reverse
      Vector

<400> SEQUENCE: 10
aactggtaat ggtagcgacc                                                20

<210> SEQ ID NO 11
<211> LENGTH: 26
<212> TYPE: DNA
<213> ORGANISM: Artificial
<220> FEATURE:
<223> OTHER INFORMATION: Primer WRB 1618 - Sgt2 5' KpnI Kozak

<400> SEQUENCE: 11
ggtaccatgg ataacgggag caagcc                                         26

<210> SEQ ID NO 12
<211> LENGTH: 30
<212> TYPE: DNA
<213> ORGANISM: Artificial
<220> FEATURE:
<223> OTHER INFORMATION: Primer WRB 1619 - Sgt2 3' KpnI native stop

<400> SEQUENCE: 12
ggtaccgttg ttaatccatg atcttcaatg                                     30

<210> SEQ ID NO 13
<211> LENGTH: 29
<212> TYPE: DNA
<213> ORGANISM: Artificial
<220> FEATURE:
<223> OTHER INFORMATION: Primer WRB 1623 - Sgt2 3' XhoI read through
      fusion

<400> SEQUENCE: 13
ctcgagatcc atgatcttca atgaagaag                                      29

<210> SEQ ID NO 14
<211> LENGTH: 1486
```

```
<212> TYPE: DNA
<213> ORGANISM: Solanum Tuberosum Sgt2.1 CDS K1
<220> FEATURE:
<221> NAME/KEY: CDS
<222> LOCATION: (7)..(1476)

<400> SEQUENCE: 14
```

| | | | | | | | | | | | | | | | |
|---|---|---|---|---|---|---|---|---|---|---|---|---|---|---|---|
| ggtacc | atg | gat | aac | ggg | agc | aag | caa | cta | cat | gtc | ctc | ttc | ctt | cct | 48 |
| | Met | Asp | Asn | Gly | Ser | Lys | Gln | Leu | His | Val | Leu | Phe | Leu | Pro | |
| | 1 | | | 5 | | | | | 10 | | | | | | |
| tac | ttc | gcc | act | ggt | cat | atc | att | cca | tta | gtt | aac | gct | gcc | agg | cta | 96 |
| Tyr | Phe | Ala | Thr | Gly | His | Ile | Ile | Pro | Leu | Val | Asn | Ala | Ala | Arg | Leu |
| 15 | | | | 20 | | | | | 25 | | | | | 30 | |
| ttc | gcc | tcc | cgt | gac | ggt | gtc | aaa | gtt | acc | atc | ctc | act | acc | cac | cac | 144 |
| Phe | Ala | Ser | Arg | Asp | Gly | Val | Lys | Val | Thr | Ile | Leu | Thr | Thr | His | His |
| | | | 35 | | | | | 40 | | | | | 45 | | |
| aat | gct | tcc | ctc | ttc | cga | tct | tct | att | gac | aat | tcc | cta | atc | tct | atc | 192 |
| Asn | Ala | Ser | Leu | Phe | Arg | Ser | Ser | Ile | Asp | Asn | Ser | Leu | Ile | Ser | Ile |
| | | 50 | | | | | 55 | | | | | 60 | | | |
| gtt | act | ctt | aag | ttc | cct | tcc | act | gaa | gtt | ggg | ttg | cct | gaa | ggg | atc | 240 |
| Val | Thr | Leu | Lys | Phe | Pro | Ser | Thr | Glu | Val | Gly | Leu | Pro | Glu | Gly | Ile |
| 65 | | | | | 70 | | | | | 75 | | | | | |
| gaa | aat | ttc | agc | tcc | gcc | tct | tca | act | gaa | atc | gcg | ggc | aaa | gta | ttt | 288 |
| Glu | Asn | Phe | Ser | Ser | Ala | Ser | Ser | Thr | Glu | Ile | Ala | Gly | Lys | Val | Phe |
| | 80 | | | | | 85 | | | | | 90 | | | | |
| ggc | ggc | aca | tat | ctt | ctg | cag | aaa | cca | atg | gaa | gat | aaa | att | cgt | gaa | 336 |
| Gly | Gly | Thr | Tyr | Leu | Leu | Gln | Lys | Pro | Met | Glu | Asp | Lys | Ile | Arg | Glu |
| 95 | | | | 100 | | | | | 105 | | | | | 110 | |
| atc | cat | cct | gat | tgt | atc | ttc | tct | gat | atg | tat | ttc | cca | tgg | act | gtc | 384 |
| Ile | His | Pro | Asp | Cys | Ile | Phe | Ser | Asp | Met | Tyr | Phe | Pro | Trp | Thr | Val |
| | | | 115 | | | | | 120 | | | | | 125 | | |
| gat | att | gcc | ctg | gag | ctc | aaa | atc | ccc | agg | cta | ttg | ttc | aac | caa | tct | 432 |
| Asp | Ile | Ala | Leu | Glu | Leu | Lys | Ile | Pro | Arg | Leu | Leu | Phe | Asn | Gln | Ser |
| | | 130 | | | | | 135 | | | | | 140 | | | |
| agc | tac | atg | tac | aat | tcc | att | ctg | tat | aat | ctt | agg | ctt | tac | aaa | cct | 480 |
| Ser | Tyr | Met | Tyr | Asn | Ser | Ile | Leu | Tyr | Asn | Leu | Arg | Leu | Tyr | Lys | Pro |
| | 145 | | | | | 150 | | | | | 155 | | | | |
| cat | gaa | aaa | ctc | atc | aat | cag | atg | gaa | tat | tcc | aaa | agt | act | aat | ttc | 528 |
| His | Glu | Lys | Leu | Ile | Asn | Gln | Met | Glu | Tyr | Ser | Lys | Ser | Thr | Asn | Phe |
| 160 | | | | | 165 | | | | | 170 | | | | | |
| tcg | gtt | ccg | gat | tta | cct | gat | aag | atc | gag | ttc | aag | cta | tcg | caa | ctt | 576 |
| Ser | Val | Pro | Asp | Leu | Pro | Asp | Lys | Ile | Glu | Phe | Lys | Leu | Ser | Gln | Leu |
| 175 | | | | 180 | | | | | 185 | | | | | 190 | |
| aca | gac | gat | ctg | gta | agg | cct | gcg | gat | gag | agg | aat | gct | ttt | gat | gaa | 624 |
| Thr | Asp | Asp | Leu | Val | Arg | Pro | Ala | Asp | Glu | Arg | Asn | Ala | Phe | Asp | Glu |
| | | | 195 | | | | | 200 | | | | | 205 | | |
| ttg | ctc | gat | cga | acc | aga | gaa | tct | gag | gat | cta | agc | tac | gga | atc | gtt | 672 |
| Leu | Leu | Asp | Arg | Thr | Arg | Glu | Ser | Glu | Asp | Leu | Ser | Tyr | Gly | Ile | Val |
| | | 210 | | | | | 215 | | | | | 220 | | | |
| cat | gat | act | ttt | tac | gag | cta | gaa | cct | gcc | tac | gct | gac | tac | tat | cag | 720 |
| His | Asp | Thr | Phe | Tyr | Glu | Leu | Glu | Pro | Ala | Tyr | Ala | Asp | Tyr | Tyr | Gln |
| | 225 | | | | | 230 | | | | | 235 | | | | |
| aag | atg | aag | aaa | acc | aaa | tgt | tgg | caa | att | ggt | ccc | att | tcc | tat | ttt | 768 |
| Lys | Met | Lys | Lys | Thr | Lys | Cys | Trp | Gln | Ile | Gly | Pro | Ile | Ser | Tyr | Phe |
| 240 | | | | | 245 | | | | | 250 | | | | | |
| tct | tcc | aaa | tta | tcc | cca | aga | aaa | gaa | ctg | att | aat | tct | tct | gat | gaa | 816 |
| Ser | Ser | Lys | Leu | Ser | Pro | Arg | Lys | Glu | Leu | Ile | Asn | Ser | Ser | Asp | Glu |
| 255 | | | | 260 | | | | | 265 | | | | | 270 | |
| agt | aac | tca | tct | gcc | gtt | gtt | gta | gag | tgg | ttg | aat | aaa | cat | aag | cac | 864 |
| Ser | Asn | Ser | Ser | Ala | Val | Val | Val | Glu | Trp | Leu | Asn | Lys | His | Lys | His |
| | | | 275 | | | | | 280 | | | | | 285 | | |

```
aaa tcg gtc ctc tac gtc tct ttt ggg agc aca att aga ttc cca gag    912
Lys Ser Val Leu Tyr Val Ser Phe Gly Ser Thr Ile Arg Phe Pro Glu
        290                 295                 300 gag caa ctc gct gaa atc gca aaa gct cta gaa gct tct acc gtc cct    960
Glu Gln Leu Ala Glu Ile Ala Lys Ala Leu Glu Ala Ser Thr Val Pro
                305                 310                 315 ttc att tgg gta gta aac aaa gac caa tta gca aaa acc acg tgg tta   1008
Phe Ile Trp Val Val Asn Lys Asp Gln Leu Ala Lys Thr Thr Trp Leu
320                 325                 330 ccg gag agt ttg ttc gat gag aaa aaa tgt ctg att att aaa ggg tgg   1056
Pro Glu Ser Leu Phe Asp Glu Lys Lys Cys Leu Ile Ile Lys Gly Trp
335                 340                 345                 350 gca ccg caa cta tcc atc tta gat cat tca gca gtc gga gga ttc atg   1104
Ala Pro Gln Leu Ser Ile Leu Asp His Ser Ala Val Gly Gly Phe Met
            355                 360                 365 aca cac tgt ggt tgg aat tca gtg ctt gaa gcc atc atc gct ggg gtg   1152
Thr His Cys Gly Trp Asn Ser Val Leu Glu Ala Ile Ile Ala Gly Val
        370                 375                 380 ccg ttg gtg acg tgg cca gtg ttc gct gaa caa ttc tac aat gaa aaa   1200
Pro Leu Val Thr Trp Pro Val Phe Ala Glu Gln Phe Tyr Asn Glu Lys
                385                 390                 395 cta gtg gag gtt atg ggg cta gga gtg aaa gta ggg gca gaa gta tat   1248
Leu Val Glu Val Met Gly Leu Gly Val Lys Val Gly Ala Glu Val Tyr
400                 405                 410 aac acc aac gga ggt gct gag ata tcg acc cct gtg tta agg agc gaa   1296
Asn Thr Asn Gly Gly Ala Glu Ile Ser Thr Pro Val Leu Arg Ser Glu
415                 420                 425                 430 aag ata aaa gaa gca att gag agg tta atg gaa agt cag aaa ata aga   1344
Lys Ile Lys Glu Ala Ile Glu Arg Leu Met Glu Ser Gln Lys Ile Arg
            435                 440                 445 gag aaa gca gtg agt atg agt aag atg gct aaa aat gca gtg gaa gaa   1392
Glu Lys Ala Val Ser Met Ser Lys Met Ala Lys Asn Ala Val Glu Glu
        450                 455                 460 ggt gga tct tca tcg aac aat ctt acc gca ctt ata gat gat atc aag   1440
Gly Gly Ser Ser Ser Asn Asn Leu Thr Ala Leu Ile Asp Asp Ile Lys
                465                 470                 475 aat ttt act tct tct tca ttg aag atc atg gat taa caacggtacc        1486
Asn Phe Thr Ser Ser Ser Leu Lys Ile Met Asp
480                 485

<210> SEQ ID NO 15
<211> LENGTH: 489
<212> TYPE: PRT
<213> ORGANISM: Solanum Tuberosum Sgt2.1 CDS K1

<400> SEQUENCE: 15

Met Asp Asn Gly Ser Lys Gln Leu His Val Leu Phe Leu Pro Tyr Phe
1               5                   10                  15

Ala Thr Gly His Ile Ile Pro Leu Val Asn Ala Ala Arg Leu Phe Ala
                20                  25                  30

Ser Arg Asp Gly Val Lys Val Thr Ile Leu Thr Thr His His Asn Ala
            35                  40                  45

Ser Leu Phe Arg Ser Ser Ile Asp Asn Ser Leu Ile Ser Ile Val Thr
        50                  55                  60

Leu Lys Phe Pro Ser Thr Glu Val Gly Leu Pro Glu Gly Ile Glu Asn
65                  70                  75                  80

Phe Ser Ser Ala Ser Ser Thr Glu Ile Ala Gly Lys Val Phe Gly Gly
                85                  90                  95
```

```
Thr Tyr Leu Leu Gln Lys Pro Met Glu Asp Lys Ile Arg Glu Ile His
            100                 105                 110
Pro Asp Cys Ile Phe Ser Asp Met Tyr Phe Pro Trp Thr Val Asp Ile
        115                 120                 125
Ala Leu Glu Leu Lys Ile Pro Arg Leu Leu Phe Asn Gln Ser Ser Tyr
    130                 135                 140
Met Tyr Asn Ser Ile Leu Tyr Asn Leu Arg Leu Tyr Lys Pro His Glu
145                 150                 155                 160
Lys Leu Ile Asn Gln Met Glu Tyr Ser Lys Ser Thr Asn Phe Ser Val
                165                 170                 175
Pro Asp Leu Pro Asp Lys Ile Glu Phe Lys Leu Ser Gln Leu Thr Asp
            180                 185                 190
Asp Leu Val Arg Pro Ala Asp Glu Arg Asn Ala Phe Asp Glu Leu Leu
        195                 200                 205
Asp Arg Thr Arg Glu Ser Glu Asp Leu Ser Tyr Gly Ile Val His Asp
    210                 215                 220
Thr Phe Tyr Glu Leu Glu Pro Ala Tyr Ala Asp Tyr Gln Lys Met
225                 230                 235                 240
Lys Lys Thr Lys Cys Trp Gln Ile Gly Pro Ile Ser Tyr Phe Ser Ser
                245                 250                 255
Lys Leu Ser Pro Arg Lys Glu Leu Ile Asn Ser Ser Asp Glu Ser Asn
            260                 265                 270
Ser Ser Ala Val Val Glu Trp Leu Asn Lys His Lys His Lys Ser
        275                 280                 285
Val Leu Tyr Val Ser Phe Gly Ser Thr Ile Arg Phe Pro Glu Glu Gln
    290                 295                 300
Leu Ala Glu Ile Ala Lys Ala Leu Glu Ala Ser Thr Val Pro Phe Ile
305                 310                 315                 320
Trp Val Val Asn Lys Asp Gln Leu Ala Lys Thr Thr Trp Leu Pro Glu
                325                 330                 335
Ser Leu Phe Asp Glu Lys Lys Cys Leu Ile Ile Lys Gly Trp Ala Pro
            340                 345                 350
Gln Leu Ser Ile Leu Asp His Ser Ala Val Gly Gly Phe Met Thr His
        355                 360                 365
Cys Gly Trp Asn Ser Val Leu Glu Ala Ile Ile Ala Gly Val Pro Leu
    370                 375                 380
Val Thr Trp Pro Val Phe Ala Glu Gln Phe Tyr Asn Glu Lys Leu Val
385                 390                 395                 400
Glu Val Met Gly Leu Gly Val Lys Val Gly Ala Glu Val Tyr Asn Thr
                405                 410                 415
Asn Gly Gly Ala Glu Ile Ser Thr Pro Val Leu Arg Ser Glu Lys Ile
            420                 425                 430
Lys Glu Ala Ile Glu Arg Leu Met Glu Ser Gln Lys Ile Arg Glu Lys
        435                 440                 445
Ala Val Ser Met Ser Lys Met Ala Lys Asn Ala Val Glu Glu Gly Gly
    450                 455                 460
Ser Ser Ser Asn Asn Leu Thr Ala Leu Ile Asp Ile Lys Asn Phe
465                 470                 475                 480
Thr Ser Ser Ser Leu Lys Ile Met Asp
                485

<210> SEQ ID NO 16
<211> LENGTH: 1479
<212> TYPE: DNA
```

<213> ORGANISM: Solanum Tuberosum Sgt2.1 CDS KX16
<220> FEATURE:
<221> NAME/KEY: CDS
<222> LOCATION: (7)..(1473)

<400> SEQUENCE: 16

```
ggtacc atg gat aac ggg agc aag caa cta cat gtc ctc ttc ctt cct         48
       Met Asp Asn Gly Ser Lys Gln Leu His Val Leu Phe Leu Pro
       1               5                   10 tac ttc gcc act ggt cat atc att cca tta gtt aac gct gcc agg cta         96
Tyr Phe Ala Thr Gly His Ile Ile Pro Leu Val Asn Ala Ala Arg Leu
15                  20                  25                  30 ttc gcc tcc cgt gac ggt gtc aaa gtt acc atc ctc act acc cac cac        144
Phe Ala Ser Arg Asp Gly Val Lys Val Thr Ile Leu Thr Thr His His
                35                  40                  45 aat gct tcc ctc ttc cga tct tct att gac aat tcc cta atc tct atc        192
Asn Ala Ser Leu Phe Arg Ser Ser Ile Asp Asn Ser Leu Ile Ser Ile
            50                  55                  60 gtt act ctt aag ttc cct tcc act gaa gtt ggg ttg cct gaa ggg atc        240
Val Thr Leu Lys Phe Pro Ser Thr Glu Val Gly Leu Pro Glu Gly Ile
        65                  70                  75 gaa aat ttc agc tcc gcc tct tca act gaa atc gcg ggc aaa gta ttt        288
Glu Asn Phe Ser Ser Ala Ser Ser Thr Glu Ile Ala Gly Lys Val Phe
    80                  85                  90 ggc ggc aca tat ctt ctg cag aaa cca atg gaa gat aaa att cgt gaa        336
Gly Gly Thr Tyr Leu Leu Gln Lys Pro Met Glu Asp Lys Ile Arg Glu
95                  100                 105                 110 atc cat cct gat tgt atc ttc tct gat atg tat ttc cca tgg act gtc        384
Ile His Pro Asp Cys Ile Phe Ser Asp Met Tyr Phe Pro Trp Thr Val
                115                 120                 125 gat att gcc ctg gag ctc aaa atc ccc agg cta ttg ttc aac caa tct        432
Asp Ile Ala Leu Glu Leu Lys Ile Pro Arg Leu Leu Phe Asn Gln Ser
            130                 135                 140 agc tac atg tac aat tcc att ctg tat aat ctt agg ctt tac aaa cct        480
Ser Tyr Met Tyr Asn Ser Ile Leu Tyr Asn Leu Arg Leu Tyr Lys Pro
        145                 150                 155 cat gaa aaa ctc atc aat cag atg gaa tat tcc aaa agt act aat ttc        528
His Glu Lys Leu Ile Asn Gln Met Glu Tyr Ser Lys Ser Thr Asn Phe
    160                 165                 170 tcg gtt ccg gat tta cct gat aag atc gag ttc aag cta tcg caa ctt        576
Ser Val Pro Asp Leu Pro Asp Lys Ile Glu Phe Lys Leu Ser Gln Leu
175                 180                 185                 190 aca gac gat ctg gta agg cct gcg gat gag agg agt gct ttt gat gaa        624
Thr Asp Asp Leu Val Arg Pro Ala Asp Glu Arg Ser Ala Phe Asp Glu
                195                 200                 205 ttg ctc gat cga acc aga gaa tct gag gat cta agc tac gga atc gtt        672
Leu Leu Asp Arg Thr Arg Glu Ser Glu Asp Leu Ser Tyr Gly Ile Val
            210                 215                 220 cat gat act ttt tac gag cta gaa cct gcc tac gct gac tac tat cag        720
His Asp Thr Phe Tyr Glu Leu Glu Pro Ala Tyr Ala Asp Tyr Tyr Gln
        225                 230                 235 aag atg aag aaa acc aaa tgt tgg caa att ggt ccc att tcc tat ttt        768
Lys Met Lys Lys Thr Lys Cys Trp Gln Ile Gly Pro Ile Ser Tyr Phe
    240                 245                 250 tct tcc aaa tta tcc cca aga aaa gaa ctg att aat tct tct gat gaa        816
Ser Ser Lys Leu Ser Pro Arg Lys Glu Leu Ile Asn Ser Ser Asp Glu
255                 260                 265                 270 agt aac tca tct gcc gtt gtt gta gag tgg ttg aat aaa cat aag cac        864
Ser Asn Ser Ser Ala Val Val Val Glu Trp Leu Asn Lys His Lys His
                275                 280                 285
```

-continued

| | |
|---|---|
| aaa tcg gtc ctc tac gtc tct ttt ggg agc aca att aga ttc cca gag<br>Lys Ser Val Leu Tyr Val Ser Phe Gly Ser Thr Ile Arg Phe Pro Glu<br>     290                          295                       300 | 912 |
| gag caa ctc gct gaa atc gca aaa gct cta gaa gct tct acc gtc cct<br>Glu Gln Leu Ala Glu Ile Ala Lys Ala Leu Glu Ala Ser Thr Val Pro<br>305                       310                       315 | 960 |
| ttc att tgg gta gta aac aaa gac caa tta gca aaa acc acg tgg tta<br>Phe Ile Trp Val Val Asn Lys Asp Gln Leu Ala Lys Thr Thr Trp Leu<br>    320                       325                     330 | 1008 |
| ccg gag agt ttg ttc gat gag aaa aaa tgt ctg att att aaa ggg tgg<br>Pro Glu Ser Leu Phe Asp Glu Lys Lys Cys Leu Ile Ile Lys Gly Trp<br>335                     340                      345                   350 | 1056 |
| gca ccg caa cta tcc atc tta gat cat tca gca gtc gga gga ttc atg<br>Ala Pro Gln Leu Ser Ile Leu Asp His Ser Ala Val Gly Gly Phe Met<br>               355                       360                   365 | 1104 |
| aca cac tgt ggt tgg aat tca gtg ctt gaa gcc atc atc gct ggg gtg<br>Thr His Cys Gly Trp Asn Ser Val Leu Glu Ala Ile Ile Ala Gly Val<br>           370                      375                   380 | 1152 |
| ccg ttg gtg acg tgg cca gtg ttc gct gaa caa ttc tac aat gaa aaa<br>Pro Leu Val Thr Trp Pro Val Phe Ala Glu Gln Phe Tyr Asn Glu Lys<br>385                     390                      395 | 1200 |
| cta gtg gag gtt atg ggg cta gga gtg aaa gta ggg gca gaa gta tat<br>Leu Val Glu Val Met Gly Leu Gly Val Lys Val Gly Ala Glu Val Tyr<br>    400                       405                     410 | 1248 |
| aac acc aac gga ggt gct gag ata tcg acc cct gtg tta agg agc gaa<br>Asn Thr Asn Gly Gly Ala Glu Ile Ser Thr Pro Val Leu Arg Ser Glu<br>415                     420                      425                 430 | 1296 |
| aag ata aaa gaa gca att gag agg tta atg gaa agt cag aaa ata aga<br>Lys Ile Lys Glu Ala Ile Glu Arg Leu Met Glu Ser Gln Lys Ile Arg<br>               435                       440                   445 | 1344 |
| gag aaa gca gtg agt atg agt aag atg gct aaa aat gca gtg gaa gaa<br>Glu Lys Ala Val Ser Met Ser Lys Met Ala Lys Asn Ala Val Glu Glu<br>           450                       455                   460 | 1392 |
| ggt gga tct tca tcg aac aat ctt acc gca ctt ata gat gat atc aag<br>Gly Gly Ser Ser Ser Asn Asn Leu Thr Ala Leu Ile Asp Asp Ile Lys<br>465                     470                      475 | 1440 |
| aat ttt act tct tct tca ttg aag atc atg gat ctcgag<br>Asn Phe Thr Ser Ser Ser Leu Lys Ile Met Asp<br>    480                       485 | 1479 |

<210> SEQ ID NO 17
<211> LENGTH: 489
<212> TYPE: PRT
<213> ORGANISM: Solanum Tuberosum Sgt2.1 CDS KX16

<400> SEQUENCE: 17

Met Asp Asn Gly Ser Lys Gln Leu His Val Leu Phe Leu Pro Tyr Phe
1               5                   10                  15

Ala Thr Gly His Ile Ile Pro Leu Val Asn Ala Ala Arg Leu Phe Ala
            20                  25                  30

Ser Arg Asp Gly Val Lys Val Thr Ile Leu Thr Thr His His Asn Ala
        35                  40                  45

Ser Leu Phe Arg Ser Ser Ile Asp Asn Ser Leu Ile Ser Ile Val Thr
    50                  55                  60

Leu Lys Phe Pro Ser Thr Glu Val Gly Leu Pro Glu Gly Ile Glu Asn
65                  70                  75                  80

Phe Ser Ser Ala Ser Ser Thr Glu Ile Ala Gly Lys Val Phe Gly Gly
                85                  90                  95

Thr Tyr Leu Leu Gln Lys Pro Met Glu Asp Lys Ile Arg Glu Ile His

```
                    100                 105                 110
Pro Asp Cys Ile Phe Ser Asp Met Tyr Phe Pro Trp Thr Val Asp Ile
            115                 120                 125

Ala Leu Glu Leu Lys Ile Pro Arg Leu Leu Phe Asn Gln Ser Ser Tyr
130                 135                 140

Met Tyr Asn Ser Ile Leu Tyr Asn Leu Arg Leu Tyr Lys Pro His Glu
145                 150                 155                 160

Lys Leu Ile Asn Gln Met Glu Tyr Ser Lys Ser Thr Asn Phe Ser Val
                165                 170                 175

Pro Asp Leu Pro Asp Lys Ile Glu Phe Lys Leu Ser Gln Leu Thr Asp
            180                 185                 190

Asp Leu Val Arg Pro Ala Asp Glu Arg Ser Ala Phe Asp Glu Leu Leu
            195                 200                 205

Asp Arg Thr Arg Glu Ser Glu Asp Leu Ser Tyr Gly Ile Val His Asp
210                 215                 220

Thr Phe Tyr Glu Leu Glu Pro Ala Tyr Ala Asp Tyr Tyr Gln Lys Met
225                 230                 235                 240

Lys Lys Thr Lys Cys Trp Gln Ile Gly Pro Ile Ser Tyr Phe Ser Ser
                245                 250                 255

Lys Leu Ser Pro Arg Lys Glu Leu Ile Asn Ser Ser Asp Glu Ser Asn
            260                 265                 270

Ser Ser Ala Val Val Glu Trp Leu Asn Lys His Lys His Lys Ser
            275                 280                 285

Val Leu Tyr Val Ser Phe Gly Ser Thr Ile Arg Phe Pro Glu Glu Gln
            290                 295                 300

Leu Ala Glu Ile Ala Lys Ala Leu Glu Ala Ser Thr Val Pro Phe Ile
305                 310                 315                 320

Trp Val Val Asn Lys Asp Gln Leu Ala Lys Thr Thr Trp Leu Pro Glu
                325                 330                 335

Ser Leu Phe Asp Glu Lys Lys Cys Leu Ile Ile Lys Gly Trp Ala Pro
            340                 345                 350

Gln Leu Ser Ile Leu Asp His Ser Ala Val Gly Gly Phe Met Thr His
            355                 360                 365

Cys Gly Trp Asn Ser Val Leu Glu Ala Ile Ala Gly Val Pro Leu
370                 375                 380

Val Thr Trp Pro Val Phe Ala Glu Gln Phe Tyr Asn Glu Lys Leu Val
385                 390                 395                 400

Glu Val Met Gly Leu Gly Val Lys Val Gly Ala Glu Val Tyr Asn Thr
                405                 410                 415

Asn Gly Gly Ala Glu Ile Ser Thr Pro Val Leu Arg Ser Glu Lys Ile
            420                 425                 430

Lys Glu Ala Ile Glu Arg Leu Met Glu Ser Gln Lys Ile Arg Glu Lys
            435                 440                 445

Ala Val Ser Met Ser Lys Met Ala Lys Asn Ala Val Glu Glu Gly Gly
            450                 455                 460

Ser Ser Ser Asn Asn Leu Thr Ala Leu Ile Asp Asp Ile Lys Asn Phe
465                 470                 475                 480

Thr Ser Ser Ser Leu Lys Ile Met Asp
                485

<210> SEQ ID NO 18
<211> LENGTH: 1614
<212> TYPE: DNA
<213> ORGANISM: Solanum Tuberosum Sgt1
```

```
<220> FEATURE:
<221> NAME/KEY: CDS
<222> LOCATION: (30)..(1496)

<400> SEQUENCE: 18
gaaacaacaa ctgttcttgg gtagtaaaa atg gta gca acc tgc aac aat ggc       53
                                 Met Val Ala Thr Cys Asn Asn Gly
                                  1               5 gaa atc ctc cat gtt ctt ttc ctt ccc ttc tta tcc gct ggt cat ttc      101
Glu Ile Leu His Val Leu Phe Leu Pro Phe Leu Ser Ala Gly His Phe
         10                  15                  20 atc cca tta gtt aac gcc gca agg cta ttc gcc tcc cgc ggt gtt aaa      149
Ile Pro Leu Val Asn Ala Ala Arg Leu Phe Ala Ser Arg Gly Val Lys
 25                  30                  35                  40 gcc aca atc ctc act acc cct cat aat gcc tta ctt ttt aga tct act      197
Ala Thr Ile Leu Thr Thr Pro His Asn Ala Leu Leu Phe Arg Ser Thr
                 45                  50                  55 att gac gat gat gtt cga att tcc gga ttt ccc att tct atc gta act      245
Ile Asp Asp Asp Val Arg Ile Ser Gly Phe Pro Ile Ser Ile Val Thr
             60                  65                  70 att aaa ttc ccc tct gct gaa gtt ggg ttg cct gaa gga att gag agc      293
Ile Lys Phe Pro Ser Ala Glu Val Gly Leu Pro Glu Gly Ile Glu Ser
         75                  80                  85 ttt aac tct gcc act tca cct gaa atg cct cat aaa att ttt tat gct      341
Phe Asn Ser Ala Thr Ser Pro Glu Met Pro His Lys Ile Phe Tyr Ala
     90                  95                 100 ctt tct ctt cta caa aag cca atg gaa gat aaa att cgt gaa ctc cgt      389
Leu Ser Leu Leu Gln Lys Pro Met Glu Asp Lys Ile Arg Glu Leu Arg
105                 110                 115                 120 cct gat tgc att ttt tct gat atg tac ttc cct tgg aca gta gat att      437
Pro Asp Cys Ile Phe Ser Asp Met Tyr Phe Pro Trp Thr Val Asp Ile
                125                 130                 135 gct gat gag ctt cac atc cct cgt att ttg tac aat ttg tct gct tac      485
Ala Asp Glu Leu His Ile Pro Arg Ile Leu Tyr Asn Leu Ser Ala Tyr
            140                 145                 150 atg tgc tac agc att atg cac aac ctt aag gtt tac aga cct cac aag      533
Met Cys Tyr Ser Ile Met His Asn Leu Lys Val Tyr Arg Pro His Lys
        155                 160                 165 cag cct aat cta gac gaa tct caa agt ttc gtg gtt cct ggt tta cct      581
Gln Pro Asn Leu Asp Glu Ser Gln Ser Phe Val Val Pro Gly Leu Pro
    170                 175                 180 gat gag ata aag ttc aag tta tcc caa ctg aca gat gat ctg aga aag      629
Asp Glu Ile Lys Phe Lys Leu Ser Gln Leu Thr Asp Asp Leu Arg Lys
185                 190                 195                 200 tcg gat gac caa aag act gtt ttt gac gaa ttg ctc gaa caa gtt gaa      677
Ser Asp Asp Gln Lys Thr Val Phe Asp Glu Leu Leu Glu Gln Val Glu
                205                 210                 215 gat tcg gag gaa cga agc tat ggc att gtt cat gat aca ttt tat gag      725
Asp Ser Glu Glu Arg Ser Tyr Gly Ile Val His Asp Thr Phe Tyr Glu
            220                 225                 230 cta gaa cct gca tat gtt gac tac tac cag aaa tta aag aaa cca aaa      773
Leu Glu Pro Ala Tyr Val Asp Tyr Tyr Gln Lys Leu Lys Lys Pro Lys
        235                 240                 245 tgt tgg cat ttt ggt ccg ctc tct cat ttt gca tcc aaa atc cgt agt      821
Cys Trp His Phe Gly Pro Leu Ser His Phe Ala Ser Lys Ile Arg Ser
    250                 255                 260 aag gaa cta att tct gag cat aac aac aat gag att gtt ata gat tgg      869
Lys Glu Leu Ile Ser Glu His Asn Asn Asn Glu Ile Val Ile Asp Trp
265                 270                 275                 280 ttg aat gca cag aaa cct aaa tcg gtt ctc tat gta tct ttc gga agc      917
Leu Asn Ala Gln Lys Pro Lys Ser Val Leu Tyr Val Ser Phe Gly Ser
```

```
                    Leu Asn Ala Gln Lys Pro Lys Ser Val Leu Tyr Val Ser Phe Gly Ser
                                    285                 290                 295 atg gct aga ttt cct gag agc caa ctg aat gaa ata gcc caa gct ctg              965
Met Ala Arg Phe Pro Glu Ser Gln Leu Asn Glu Ile Ala Gln Ala Leu
                300                 305                 310 gat gct tca aat gtt cct ttc att ttt gta ttg agg cct aat gaa gaa             1013
Asp Ala Ser Asn Val Pro Phe Ile Phe Val Leu Arg Pro Asn Glu Glu
                315                 320                 325 acg gcg tcg tgg ttg cca gtt ggt aat tta gag gac aag act aaa aag             1061
Thr Ala Ser Trp Leu Pro Val Gly Asn Leu Glu Asp Lys Thr Lys Lys
            330                 335                 340 ggt ttg tac atc aaa ggg tgg gtc cca cag ctt acg atc atg gaa cat             1109
Gly Leu Tyr Ile Lys Gly Trp Val Pro Gln Leu Thr Ile Met Glu His
345                 350                 355                 360 tca gca aca ggc ggg ttc atg act cat tgt ggt act aat tcg gtt ctg             1157
Ser Ala Thr Gly Gly Phe Met Thr His Cys Gly Thr Asn Ser Val Leu
                365                 370                 375 gaa gcc atc act ttt ggc gtg cca atg ata aca tgg cca ctt tat gct             1205
Glu Ala Ile Thr Phe Gly Val Pro Met Ile Thr Trp Pro Leu Tyr Ala
                380                 385                 390 gat caa ttc tac aac gag aag gta gtc gag gtt agg gga ttg gga atc             1253
Asp Gln Phe Tyr Asn Glu Lys Val Val Glu Val Arg Gly Leu Gly Ile
                395                 400                 405 aaa atc ggg ata gat gta tgg aat gaa ggg att gag atc acg ggc cct             1301
Lys Ile Gly Ile Asp Val Trp Asn Glu Gly Ile Glu Ile Thr Gly Pro
            410                 415                 420 gta ata gaa agc gcc aag att aga gaa gca att gag aga cta atg atc             1349
Val Ile Glu Ser Ala Lys Ile Arg Glu Ala Ile Glu Arg Leu Met Ile
425                 430                 435                 440 agt aat ggt tct gag gaa att ata aat att agg gat aga gta atg gct             1397
Ser Asn Gly Ser Glu Glu Ile Ile Asn Ile Arg Asp Arg Val Met Ala
                445                 450                 455 atg agc aaa atg gct cag aat gca aca aat gaa ggt gga tct tcg tgg             1445
Met Ser Lys Met Ala Gln Asn Ala Thr Asn Glu Gly Gly Ser Ser Trp
                460                 465                 470 aac aat ctc act gct ctc att caa cat atc aag aat tat aat ctt aat             1493
Asn Asn Leu Thr Ala Leu Ile Gln His Ile Lys Asn Tyr Asn Leu Asn
            475                 480                 485 tag ttggaagaca gaaataagtc cttgcattgt aacttggtgt gtgtgtgtgt                  1546
tttttttcca cttaataaaa tgaaggaatg gatggatgga tcttaacttt aaaaaaaaaa           1606
aaaaaaaa                                                                   1614

<210> SEQ ID NO 19
<211> LENGTH: 488
<212> TYPE: PRT
<213> ORGANISM: Solanum Tuberosum Sgt1

<400> SEQUENCE: 19

Met Val Ala Thr Cys Asn Asn Gly Glu Ile Leu His Val Leu Phe Leu
1               5                   10                  15

Pro Phe Leu Ser Ala Gly His Phe Ile Pro Leu Val Asn Ala Ala Arg
                20                  25                  30

Leu Phe Ala Ser Arg Gly Val Lys Ala Thr Ile Leu Thr Thr Pro His
            35                  40                  45

Asn Ala Leu Leu Phe Arg Ser Thr Ile Asp Asp Val Arg Ile Ser
        50                  55                  60

Gly Phe Pro Ile Ser Ile Val Thr Ile Lys Phe Pro Ser Ala Glu Val
65                  70                  75                  80
```

-continued

```
Gly Leu Pro Glu Gly Ile Glu Ser Phe Asn Ser Ala Thr Ser Pro Glu
                85                  90                  95
Met Pro His Lys Ile Phe Tyr Ala Leu Ser Leu Leu Gln Lys Pro Met
            100                 105                 110
Glu Asp Lys Ile Arg Glu Leu Arg Pro Asp Cys Ile Phe Ser Asp Met
        115                 120                 125
Tyr Phe Pro Trp Thr Val Asp Ile Ala Asp Glu Leu His Ile Pro Arg
    130                 135                 140
Ile Leu Tyr Asn Leu Ser Ala Tyr Met Cys Tyr Ser Ile Met His Asn
145                 150                 155                 160
Leu Lys Val Tyr Arg Pro His Lys Gln Pro Asn Leu Asp Glu Ser Gln
                165                 170                 175
Ser Phe Val Pro Gly Leu Pro Asp Glu Ile Lys Phe Lys Leu Ser
            180                 185                 190
Gln Leu Thr Asp Asp Leu Arg Lys Ser Asp Gln Lys Thr Val Phe
        195                 200                 205
Asp Glu Leu Leu Glu Gln Val Glu Asp Ser Glu Glu Arg Ser Tyr Gly
    210                 215                 220
Ile Val His Asp Thr Phe Tyr Glu Leu Glu Pro Ala Tyr Val Asp Tyr
225                 230                 235                 240
Tyr Gln Lys Leu Lys Lys Pro Lys Cys Trp His Phe Gly Pro Leu Ser
                245                 250                 255
His Phe Ala Ser Lys Ile Arg Ser Lys Glu Leu Ile Ser Glu His Asn
            260                 265                 270
Asn Asn Glu Ile Val Ile Asp Trp Leu Asn Ala Gln Lys Pro Lys Ser
        275                 280                 285
Val Leu Tyr Val Ser Phe Gly Ser Met Ala Arg Phe Pro Glu Ser Gln
    290                 295                 300
Leu Asn Glu Ile Ala Gln Ala Leu Asp Ala Ser Asn Val Pro Phe Ile
305                 310                 315                 320
Phe Val Leu Arg Pro Asn Glu Glu Thr Ala Ser Trp Leu Pro Val Gly
                325                 330                 335
Asn Leu Glu Asp Lys Thr Lys Lys Gly Leu Tyr Ile Lys Gly Trp Val
            340                 345                 350
Pro Gln Leu Thr Ile Met Glu His Ser Ala Thr Gly Gly Phe Met Thr
        355                 360                 365
His Cys Gly Thr Asn Ser Val Leu Glu Ala Ile Thr Phe Gly Val Pro
    370                 375                 380
Met Ile Thr Trp Pro Leu Tyr Ala Asp Gln Phe Tyr Asn Glu Lys Val
385                 390                 395                 400
Val Glu Val Arg Gly Leu Gly Ile Lys Ile Gly Ile Asp Val Trp Asn
                405                 410                 415
Glu Gly Ile Glu Ile Thr Gly Pro Val Ile Glu Ser Ala Lys Ile Arg
            420                 425                 430
Glu Ala Ile Glu Arg Leu Met Ile Ser Asn Gly Ser Glu Glu Ile Ile
        435                 440                 445
Asn Ile Arg Asp Arg Val Met Ala Met Ser Lys Met Ala Gln Asn Ala
    450                 455                 460
Thr Asn Glu Gly Gly Ser Ser Trp Asn Asn Leu Thr Ala Leu Ile Gln
465                 470                 475                 480
His Ile Lys Asn Tyr Asn Leu Asn
                485
```

<210> SEQ ID NO 20
<211> LENGTH: 1458
<212> TYPE: DNA
<213> ORGANISM: Solanum tuberosum Sgt 2.2 CDS KX10
<220> FEATURE:
<221> NAME/KEY: CDS
<222> LOCATION: (7)..(1452)

<400> SEQUENCE: 20

```
ggtacc atg gat aac ggg agc aag caa cta cac gtc ctc ttc ctt cct         48
       Met Asp Asn Gly Ser Lys Gln Leu His Val Leu Phe Leu Pro
         1               5                  10 tac ttc gcc act ggt cat atc att cca tta gtt aac gct gcc agg cta         96
Tyr Phe Ala Thr Gly His Ile Ile Pro Leu Val Asn Ala Ala Arg Leu
 15                  20                  25                  30 ttc gcc tcc cgt ggc ggt gtc aaa gtt acc att ctc act acc cac cac        144
Phe Ala Ser Arg Gly Gly Val Lys Val Thr Ile Leu Thr Thr His His
                 35                  40                  45 aat gct tcc ctc ttc cga tct tct att gac aat tcc cta atc tct atc        192
Asn Ala Ser Leu Phe Arg Ser Ser Ile Asp Asn Ser Leu Ile Ser Ile
     50                  55                  60 gct act ctt aag ttc cct tcc act gaa gtt ggg ttg cct gaa ggg atc        240
Ala Thr Leu Lys Phe Pro Ser Thr Glu Val Gly Leu Pro Glu Gly Ile
 65                  70                  75 gaa aat ttc agc tcc gcc tct tca act gaa atc gcg agc aaa tta ttt        288
Glu Asn Phe Ser Ser Ala Ser Ser Thr Glu Ile Ala Ser Lys Leu Phe
             80                  85                  90 ggc ggc att tat ctt ctg cag aaa cca atg gaa gat aaa att cgt gaa        336
Gly Gly Ile Tyr Leu Leu Gln Lys Pro Met Glu Asp Lys Ile Arg Glu
 95                 100                 105                 110 atc cat cct gat tgt atc ttc tct gat atg tat ttc cca tgg act gtc        384
Ile His Pro Asp Cys Ile Phe Ser Asp Met Tyr Phe Pro Trp Thr Val
                115                 120                 125 gat att gca ctg gag ctc aaa atc ccc agg cta ttg ttc aac caa tct        432
Asp Ile Ala Leu Glu Leu Lys Ile Pro Arg Leu Leu Phe Asn Gln Ser
            130                 135                 140 agc tac atg tac aat tcc att ctg tac aat ctt agg ctt tac aaa cct        480
Ser Tyr Met Tyr Asn Ser Ile Leu Tyr Asn Leu Arg Leu Tyr Lys Pro
145                 150                 155 cac gaa tat tcc aaa agt agt aat ttc tcg gtt ccg ggt tta cct gat        528
His Glu Tyr Ser Lys Ser Ser Asn Phe Ser Val Pro Gly Leu Pro Asp
    160                 165                 170 aag atc gag ttc aat cta tcg caa ctt aca gac gat ctg ata aag cct        576
Lys Ile Glu Phe Asn Leu Ser Gln Leu Thr Asp Asp Leu Ile Lys Pro
175                 180                 185                 190 gca gat gag agg aat ggt ttt gat gaa ttg ctc gat cga acc aga gaa        624
Ala Asp Glu Arg Asn Gly Phe Asp Glu Leu Leu Asp Arg Thr Arg Glu
                195                 200                 205 tct gag gat caa agc tac ggt atc gtt cat gat act ttt tac gaa cta        672
Ser Glu Asp Gln Ser Tyr Gly Ile Val His Asp Thr Phe Tyr Glu Leu
            210                 215                 220 gaa cct gcc tac gct gac tac tat cag aag atg aag aaa acc aaa tgt        720
Glu Pro Ala Tyr Ala Asp Tyr Tyr Gln Lys Met Lys Lys Thr Lys Cys
            225                 230                 235 tgg caa att ggt ccc att tcc tat ttt tct tcc aaa tta ttc cga aga        768
Trp Gln Ile Gly Pro Ile Ser Tyr Phe Ser Ser Lys Leu Phe Arg Arg
240                 245                 250 aaa gat ctg att aat tct ttt gat gaa agt aac tca tct gcc gct gtt        816
Lys Asp Leu Ile Asn Ser Phe Asp Glu Ser Asn Ser Ser Ala Ala Val
255                 260                 265                 270
```

```
gta gag tgg ttg aat aaa cag aag cac aaa tcg gtc ctc tac gtc tct    864
Val Glu Trp Leu Asn Lys Gln Lys His Lys Ser Val Leu Tyr Val Ser
            275                 280                 285 ttc ggg agc aca gtt aaa ttc cca gag gag caa ctc gct gaa atc gca    912
Phe Gly Ser Thr Val Lys Phe Pro Glu Glu Gln Leu Ala Glu Ile Ala
        290                 295                 300 aaa gct cta gaa gct tct acc gtc cct ttc att tgg gta gtg aag gag    960
Lys Ala Leu Glu Ala Ser Thr Val Pro Phe Ile Trp Val Val Lys Glu
    305                 310                 315 gac caa tca gca aaa acc acc tgg tta ccg gag agt ttg ttc gat gag   1008
Asp Gln Ser Ala Lys Thr Thr Trp Leu Pro Glu Ser Leu Phe Asp Glu
320                 325                 330 aaa aaa ggt ctg att att aaa ggg tgg gct ccg caa cta acc atc tta   1056
Lys Lys Gly Leu Ile Ile Lys Gly Trp Ala Pro Gln Leu Thr Ile Leu
335                 340                 345                 350 gat cat tca gca gta gga gga ttc atg aca cac tgt gga tgg aat tcg   1104
Asp His Ser Ala Val Gly Gly Phe Met Thr His Cys Gly Trp Asn Ser
            355                 360                 365 gtg ctt gaa gct atc atc gct ggg gtg ccg ttg gtg acg tgg cca gtg   1152
Val Leu Glu Ala Ile Ile Ala Gly Val Pro Leu Val Thr Trp Pro Val
        370                 375                 380 ttc gct gaa caa ttc tac aat gaa aaa ctt gtg gag gtt atg gag cta   1200
Phe Ala Glu Gln Phe Tyr Asn Glu Lys Leu Val Glu Val Met Glu Leu
    385                 390                 395 gga gtg aaa gta ggg gca gaa gta cat aac tcc gac gga tgt gtt gag   1248
Gly Val Lys Val Gly Ala Glu Val His Asn Ser Asp Gly Cys Val Glu
400                 405                 410 ata tcg agc cct gtg tta agg agc gaa aag ata aaa gaa gca att gag   1296
Ile Ser Ser Pro Val Leu Arg Ser Glu Lys Ile Lys Glu Ala Ile Glu
415                 420                 425                 430 agg tta atg gaa agt cag aaa ata aga gag aaa gca gtg agt atg agt   1344
Arg Leu Met Glu Ser Gln Lys Ile Arg Glu Lys Ala Val Ser Met Ser
            435                 440                 445 aag atg gct aaa aat gca gtg gaa gaa ggt gga tct tca tgg agc aat   1392
Lys Met Ala Lys Asn Ala Val Glu Glu Gly Gly Ser Ser Trp Ser Asn
        450                 455                 460 ctt acc gca ctt ata gat gat atc aag aat ttt act tct tct tca ttg   1440
Leu Thr Ala Leu Ile Asp Asp Ile Lys Asn Phe Thr Ser Ser Ser Leu
    465                 470                 475 aag atc atg gat ctcgag                                             1458
Lys Ile Met Asp
        480

<210> SEQ ID NO 21
<211> LENGTH: 482
<212> TYPE: PRT
<213> ORGANISM: Solanum tuberosum Sgt 2.2 CDS KX10

<400> SEQUENCE: 21

Met Asp Asn Gly Ser Lys Gln Leu His Val Leu Phe Leu Pro Tyr Phe
1               5                   10                  15

Ala Thr Gly His Ile Ile Pro Leu Val Asn Ala Ala Arg Leu Phe Ala
            20                  25                  30

Ser Arg Gly Gly Val Lys Val Thr Ile Leu Thr Thr His His Asn Ala
        35                  40                  45

Ser Leu Phe Arg Ser Ser Ile Asp Asn Ser Leu Ile Ser Ile Ala Thr
    50                  55                  60

Leu Lys Phe Pro Ser Thr Glu Val Gly Leu Pro Glu Gly Ile Glu Asn
65                  70                  75                  80
```

-continued

```
Phe Ser Ser Ala Ser Ser Thr Glu Ile Ala Ser Lys Leu Phe Gly Gly
                85                  90                  95
Ile Tyr Leu Leu Gln Lys Pro Met Glu Asp Lys Ile Arg Glu Ile His
                100                 105                 110
Pro Asp Cys Ile Phe Ser Asp Met Tyr Phe Pro Trp Thr Val Asp Ile
                115                 120                 125
Ala Leu Glu Leu Lys Ile Pro Arg Leu Leu Phe Asn Gln Ser Ser Tyr
    130                 135                 140
Met Tyr Asn Ser Ile Leu Tyr Asn Leu Arg Leu Tyr Lys Pro His Glu
145                 150                 155                 160
Tyr Ser Lys Ser Ser Asn Phe Ser Val Pro Gly Leu Pro Asp Lys Ile
                165                 170                 175
Glu Phe Asn Leu Ser Gln Leu Thr Asp Asp Leu Ile Lys Pro Ala Asp
                180                 185                 190
Glu Arg Asn Gly Phe Asp Glu Leu Leu Asp Arg Thr Arg Glu Ser Glu
                195                 200                 205
Asp Gln Ser Tyr Gly Ile Val His Asp Thr Phe Tyr Glu Leu Glu Pro
    210                 215                 220
Ala Tyr Ala Asp Tyr Tyr Gln Lys Met Lys Lys Thr Lys Cys Trp Gln
225                 230                 235                 240
Ile Gly Pro Ile Ser Tyr Phe Ser Ser Lys Leu Phe Arg Arg Lys Asp
                245                 250                 255
Leu Ile Asn Ser Phe Asp Glu Ser Asn Ser Ser Ala Ala Val Val Glu
                260                 265                 270
Trp Leu Asn Lys Gln Lys His Lys Ser Val Leu Tyr Val Ser Phe Gly
                275                 280                 285
Ser Thr Val Lys Phe Pro Glu Glu Gln Leu Ala Glu Ile Ala Lys Ala
    290                 295                 300
Leu Glu Ala Ser Thr Val Pro Phe Ile Trp Val Lys Glu Asp Gln
305                 310                 315                 320
Ser Ala Lys Thr Thr Trp Leu Pro Glu Ser Leu Phe Asp Glu Lys Lys
                325                 330                 335
Gly Leu Ile Ile Lys Gly Trp Ala Pro Gln Leu Thr Ile Leu Asp His
                340                 345                 350
Ser Ala Val Gly Gly Phe Met Thr His Cys Gly Trp Asn Ser Val Leu
    355                 360                 365
Glu Ala Ile Ile Ala Gly Val Pro Leu Val Thr Trp Pro Val Phe Ala
    370                 375                 380
Glu Gln Phe Tyr Asn Glu Lys Leu Val Glu Val Met Glu Leu Gly Val
385                 390                 395                 400
Lys Val Gly Ala Glu Val His Asn Ser Asp Gly Cys Val Glu Ile Ser
                405                 410                 415
Ser Pro Val Leu Arg Ser Glu Lys Ile Lys Glu Ala Ile Glu Arg Leu
                420                 425                 430
Met Glu Ser Gln Lys Ile Arg Glu Lys Ala Val Ser Met Ser Lys Met
                435                 440                 445
Ala Lys Asn Ala Val Glu Glu Gly Gly Ser Ser Trp Ser Asn Leu Thr
    450                 455                 460
Ala Leu Ile Asp Asp Ile Lys Asn Phe Thr Ser Ser Ser Leu Lys Ile
465                 470                 475                 480
Met Asp
```

SOLANUM TUBEROSUM STEROL ALKALOID GLYCOSYLTRANSFERASE (SGT) A NOVEL SOLANIDINE GLUCOSYLTRANSFERASE SGT2 AND USES THEREOF

CROSS REFERENCE TO RELATED APPLCATION

This application is related to commonly assigned U.S. application Ser. No. 11/272,958, the disclosure of which is herein incorporated by reference in its entirety.

BACKGROUND OF THE INVENTION

1. Field of the Invention

The present invention is directed to the steroidal alkaloid glycosyl transferase enzyme UDP-glucose:solanidine glucosyltransferase (SGT2) that is involved in the biosynthesis of steroidal glycoalkaloids in Solanaceous plants. More particularly, the invention is directed to nucleic acid sequences that encode SGT2, recombinant polynucleotide molecules containing the sequences, and uses thereof. A particular use of the nucleic acid sequences and portions thereof is to inhibit SGT2 activity and reduce the levels of the steroidal glycoalkaloid α-chaconine and/or increase the levels of the steroidal glycoalkaloid α-solanine in Solanaceous plants.

2. Description of the Art

Solanaceous plants include such agronomically important crops as potato, tomato and eggplant. Many Solanaceous species, including potato, synthesize bitter tasting steroidal glycoalkaloids (nitrogen-containing steroidal glycosides) as a defense against microbial or insect pests or in response to environmental stress. Accumulation of these natural toxicants can affect food quality and safety, especially in improperly stored or processed potatoes. This has led to the implementation of a guidelines limiting glycoalkaloid content in a tuber of a given potato cultivar to 20 mg/100 gm. While the guidelines provide effective protection for the consumer, its effectiveness is dependent upon limiting the release of new cultivars for commercial production to those with acceptable glycoalkaloid levels. For potato breeding programs to develop new cultivars with improved agronomic or processing properties, the need to select also for low levels of glycoalkaloids can present a difficult problem. A method to decrease the glycoalkaloid content of any newly developed cultivar with minimum impact on other characteristics would be of great use to obtain valuable new commercial potato cultivars.

SUMMARY OF THE INVENTION

The present invention is directed to the steroidal alkaloid glycosyl transferase enzyme UDP-glucose:solanidine glucosyltransferase (SGT2) that is involved in the biosynthesis of steroidal glycoalkaloids in Solanaceous plants. More particularly, the invention is directed to nucleic acid sequences that encode SGT2, recombinant polynucleotide molecules containing the sequences, and uses thereof. A particular use of the nucleic acid sequences and portions thereof is to inhibit SGT2 activity and reduce the levels of the steroidal glycoalkaloid α-chaconine and/or increase the levels of the steroidal glycoalkaloid α-solanine in Solanaceous plants.

In cultivated potato the predominant glycoalkaloid species, α-chaconine and α-solanine, are triglycosylated derivatives of the aglycone solanidine. These steroidal glycoalkaloids contain either glucose (α-chaconine) or galactose (α-solanine) as the primary glycosyl residue. A proposed steroidal glycoalkaloid biosynthetic pathway illustrating biosynthesis of the glycoalkaloids α-chaconine and α-solanine is shown in FIG. 1. The first step in the synthesis of α-chaconine is catalyzed by SGT2. As discussed in detail herein, the present invention finds particular use to inhibit SGT2 activity and reduce the levels of the steroidal glycoalkaloid α-chaconine and/or increase the levels of the steroidal glycoalkaloid α-solanine in Solanaceous plants.

In one aspect, the present invention is directed to isolated nucleic acid molecules that encode a polypeptide having SGT2 activity. The Sgt2 gene sequence is specifically exemplified herein (SEQ ID NO:1 and NO:3). The deduced amino acid sequence is shown in SEQ ID NO:2 and NO:4.

Nucleic acid sequences having at least 99% sequence identity with the exemplified Sgt2 sequences as described in detail, below, and which encode a polypeptides having SGT2 activity are also encompassed by the present invention.

Nucleic acid sequences which hybridize specifically to the SGT2 coding sequence or its complement under high stringency conditions and which encode a polypeptide having SGT2 activity are also encompassed by the present invention.

The invention is also directed to recombinant nucleic acid molecules, the RNA equivalent, the complement of the DNA molecules, and vectors such as cloning, expression or transformation vectors comprising the nucleic acid sequences or molecules.

The invention is also directed to host cells comprising the nucleic acid sequences. The sequences may be used to encode an SGT2 polypeptide or for gene silencing methods. Such gene silencing methods include providing cells transformed with multiple copies of the sequence in the sense orientation for gene silencing, transforming the plants or plant cells with an antisense nucleotide sequence complementary to an mRNA-encoding SGT2 or other gene silencing methods as known in the art.

In particular, the invention is directed to plants or plant cells transformed with the sequences or constructs containing the sequences or fragments thereof to provide plants having reduced levels of glycoalkaloids. Such plants include, for example, Solanaceous plants. Prominent food crops are in the *Solanaceae* family. These include potato (*Solanum tuberosum*); tomato (*Lysopersicon*, e.g., *L. lycopersicum* and *L. esculentum*); pepper (*Capsicum*); eggplant (*Solanum melongena*). Most preferably, in the practice of the invention, the Solanaceous plant is potato.

Use of construction of antisense constructs containing a partial SGT2 sequence to alter glycoalkaloid biosynthesis is encompassed by the invention. This is described in detail in the Example, below.

The present invention is also directed to isolated polypeptides having SGT2 activity. SEQ ID NO:2 and NO:3 show the amino acid sequences encoded by the exemplified DNA sequences SEQ ID NO:1 and NO:2. A polypeptide having an amino acid sequence which has at least 99% sequence identity with the exemplified sequence SEQ ID NO:2 or NO:4, as described in detail, below, is encompassed by the invention. Polypeptide encoded by a nucleic acid sequence which hybridizes under high stringency conditions with the exemplified Sgt2 nucleic acid sequence as discussed in detail, below, are also encompassed by the invention. Variants of the polypeptides are encompassed by the invention as well as fragments having SGT2 activity. The activity and substrate preference of the enzyme SGT2 have not been demonstrated in vivo or in vitro prior to our invention and are demonstrated for the first time here using reverse genetics in transgenic plants and direct biochemical assay of purified recombinant protein.

Another aspect of the invention is the provision of methods of use of the sequences and enzyme. Such methods include use as probes capable of detecting the Sgt2 gene or fragment thereof, methods to obtain purified SGT2, methods for reducing steroidal glycoalkaloids in plants, methods for altering the ratio of α-solanine and α-chaconine in plants, such as the use of suppression constructs; and methods for increasing steroidal glycoalkaloids in plants by increasing expression of SGT2, and methods of increasing α-chaconine in plants, such as by increasing the copy number of the gene.

SEQ ID NO:5 shows the partial Sgt2 sequence that was used for construction of antisense constructs for generation of the transgenic plant lines. This is described in detail in the Example below.

The invention represents the first cloning of the gene encoding SGT2 and demonstration of its associated function in vivo and in vitro. One of the primary advantages of the invention is that it can provide a method to reduce the toxicity of glycoalkaloid in Solanaceous species as well as reducing the level of total glycoalkaloids in Solanaceous species. Such a method offers a wide variety of benefits extending from the farm, to processing, shipping, and finally to marketing of potatoes and potato products. The ability to reduce toxicant levels in selected varieties will allow introduction of new potato cultivars that cannot currently be released due to glycoalkaloid concentrations exceeding the acceptable level. The utilization of direct genetic modification is especially important to avoid problems of classic potato breeding programs. The genome of commercial potato cultivars grown in the United States (which are tetraploid and highly heterozygous) is exceedingly complex. This genetic complexity makes it essentially impossible for breeders to introduce a single genetic trait into an existing cultivar, while maintaining its original properties. The invention provides a means to insert a sense or antisense Sgt2 transgene into the genome of these cultivars without altering the existing genes.

Another advantage of the invention is that it provides a means of solving problems in potato storage and shipping due to glycoalkaloids. Inappropriate post-harvest handling of tubers can result in increased glycoalkaloid biosynthesis in current commercial cultivars. The modification of glycoalkaloid biosynthetic pathways is beneficial to reduce or eliminate glycoalkaloid biosynthesis during storage and shipping.

Another advantage of the invention is that alteration of the ratio of α-solanine to α-chaconine provides a means of increasing the insect resistance by elevation of α-solanine levels while reducing the toxicity to humans by reducing the α-chaconine levels even in the absence of a reduction in the levels of total glycoalkaloids.

Other objects and advantages of this invention will become readily apparent from the ensuing description.

BRIEF DESCRIPTION OF THE DRAWINGS

FIG. 2 shows the ClustalW alignment of Sgt2 (SEQ ID NO:1) and Sgt1 (SEQ ID NO:18) nucleotide sequences showing regions of identity and similarity.

FIG. 3 shows the ClustalW alignment of SGT2 (SEQ ID NO:2) and SGT1 (SEQ ID NO:19) deduced amino acid sequences showing regions of identity and similarity.

BRIEF DESCRIPTION OF THE SEQUENCES

Figure 1:
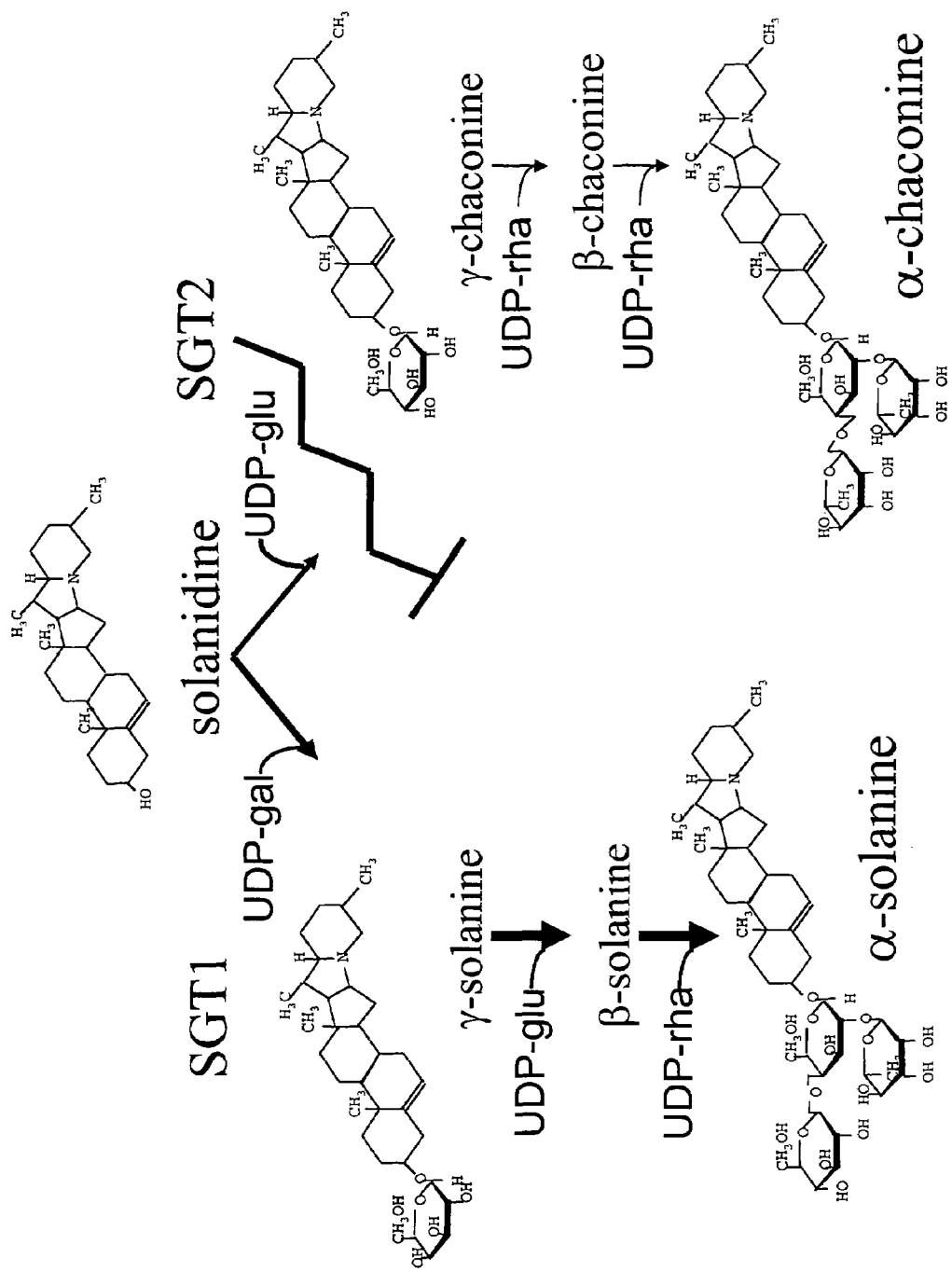
FIG. 1 shows the proposed SGA biosynthetic pathway for synthesis of α-solanine and α-chaconine, the two predominant potato steroidal glycoalkaloids from the aglycone, solanidine.

SEQ ID NO: 1 shows the cDNA sequence of the *Solanum tuberosum* SOLtu:Sgt2.1 gene. Sequence feature information: *Solanum tuberosum* Sgt2.1 cDNA sequence: nucleotide 1 to 1671; coding region: nucleotide 1 to 1470, translation initiation codon: nucleotide 1 to 3; translation termination codon: nucleotide 1468 to 1470.

SEQ ID NO:2 shows the amino acid sequence encoded by SEQ ID NO:1.

SEQ ID NO:3 shows the cDNA sequence of the *Solanum tuberosum* SOLtu:Sgt2.2 gene. Sequence feature information: *Solanum tuberosum* Sgt2.2 cDNA sequence: nucleotide 1 to 1649; coding region: nucleotide 1 to 1449, translation initiation codon: nucleotide 1 to 3; translation termination codon: nucleotide 1447 to 1449.

SEQ ID NO:4 shows the amino acid sequence encoded by SEQ ID NO:3.

SEQ ID NO:5 shows an Sgt2.1 partial sequence that was used for construction of antisense constructs for the transgenic plant lines. This is described in detail in the Example below.

SEQ ID NO:6 is primer WRB 1384-Forward.

SEQ ID NO:7 is primer WRB 1386-Forward.

SEQ ID NO:8 is primer WRB 1414-Reverse.

SEQ ID NO:9 is primer WRB 1453 Sgt2 3-prime Forward.

SEQ ID NO:10 is primer WRB 1526 PCR gt11 Rev-M13 Reverse Vector.

SEQ ID NO:11 is primer WRB 1618-Sgt2 5' KpnI Kozak.

SEQ ID NO:12 is primer WRB 1619-Sgt2 3' KpnI native stop.

SEQ ID NO:13 is primer WRB 1623-Sgt2 3' XhoI read through fusion.

SEQ ID NO:14 shows the coding sequence of the *Solanum tuberosum* Sgt2.1 CDS K1 native protein expression fragment. Sequence feature information: *Solanum tuberosum* Sgt2 cDNA fragment: nucleotide 1 to 1486; KpnI restriction endonucleases recognition site: nucleotide 1 to 6; coding region: nucleotide 7 to 14760; translation initiation codon: nucleotide 7 to 9; translation termination codon: nucleotide 1474 to 1476; KpnI restriction endonucleases recognition site: nucleotide 1481 to 1486. The Sgt2.1 CDS K1 cDNA from 7 to 1521 is 100% identical to SEQ ID NO:1

SEQ ID NO:15 shows the amino acid sequence encoded by SEQ ID NO:14. The Sgt2.1 CDS K1 translated protein is 100% identical to SEQ ID NO:2.

SEQ ID NO:16 shows the coding sequence of the *Solanum tuberosum* Sgt2.1 CDS KX16 fusion protein expression fragment. Sequence feature information: *Solanum tuberosum* Sgt2.1 cDNA fragment: nucleotide 1 to 1479; KpnI restriction endonucleases recognition site: nucleotide 1 to 6; coding region: nucleotide 7 to 1473; translation initiation codon: nucleotide 7 to 9; XhoI restriction endonucleases recognition site: nucleotide 1474 to 1479. The Sgt2.1 CDS KX16 cDNA from 7 to 1473 contains two single nucleotide polymorphisms compared to SEQ ID NO:1

SEQ ID NO:17 shows the amino acid sequence encoded by SEQ ID NO:16. The Sgt2.1 CDS KX16 translated protein is 100% identical to SEQ ID NO:2.

SEQ ID NO:18 shows the cDNA sequence of Sgt1.

SEQ ID NO:19 shows the deduced amino acid of SGT1 encoded by SEQ ID NO:18.

SEQ ID NO:20 shows the coding sequence of the *Solanum tuberosum* Sgt2.2 CDS KX10 fusion protein expression fragment. Sequence feature information: *Solanum tuberosum* Sgt2.2 cDNA fragment: nucleotide 1 to 1458; KpnI restriction endonucleases recognition site: nucleotide 1 to 6; SGT2.2 coding region: nucleotide 7 to 1452; translation initiation codon: nucleotide 7 to 9; XhoI restriction endonucleases recognition site: nucleotide 1453 to 1458. The Sgt2.2 CDS KX10 cDNA from 7 to 1458 contains a single nucleotide polymorphisms compared to SEQ ID NO:3 (An A to G at position 1388).

SEQ ID NO:21 shows the amino acid sequence encoded by SEQ ID NO:20. The Sgt2.2 CDS KX10 translated protein is 100% identical to SEQ ID NO:4.

INCORPORATION-BY-REFERENCE OF MATERIAL SUBMITTED ON A COMPACT DISC

Incorporated herein by reference in its entirety is a Sequence Listing, including SEQ ID NO:1 through SEQ ID NO:21. The Sequence Listing is contained on a compact disc, i.e., diskette, 3.5 in., two identical copies of which are filed herewith. The Sequence Listing, in IBM/PC MS-DOS format (named "McCue 014304.txt"), PatentIn Version 3.3, was recorded on Nov. 10, 2005, and is 70 kilobytes in size.

DEPOSIT OF BIOLOGICAL MATERIAL (PLASMIDS CONTAINING SEQUENCES)

*Escherichia coli* strain pYES2.1 Sgt2.2 CDS KX10, containing the Sgt2.2 CDS KX10 clone described herein was deposited on Nov. 4, 2005, under the provisions of the Budapest Treaty in the Agricultural Research Culture Collection (NRRL) in Peoria, Ill., and has been assigned Accession No. NRRL B-30886. Plasmid pYES2.1 Sgt2.2 CDS KX10 contains a sequence corresponding to SEQ ID NO:20. *Escherichia coli* strain pYES2.1 Sgt2.1 CDS KX16, containing the Sgt2.1 CDS KX16 clone described herein was deposited on Nov. 4, 2005, under the provisions of the Budapest Treaty in the Agricultural Research Culture Collection (NRRL) in Peoria, Ill., and has been assigned Accession No. NRRL B-30887. Plasmid pYES2.1 Sgt2.1 CDS KX16 contains a sequence corresponding to SEQ ID NO:16.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton, et al., Dictionary of Microbiology and Molecular Biology (2d ed. 1994); The Cambridge Dictionary of Science and Technology (Walker ed., 1988);

*The Glossary of Genetics*, 5th Ed., Rieger, R., et al. (eds.), Springer Verlag (1991); and Hale & Marham, *The Harper Collins Dictionary of Biology* (1991). References providing standard molecular biological procedures include Sambrook et al. (1989) *Molecular Cloning*, second edition, Cold Spring Harbor Laboratory, Plainview, N.Y.; *DNA Cloning*, Vols. I and II, IRL Press, Oxford, UK; and Hames and Higgins (eds.) (1985) *Nucleic Acid Hybridization*, IRL Press, Oxford, UK. References related to the manipulation and transformation of plant tissue include Kung and Arntzen (eds.) (1989) *Plant Biotechnology*, Butterworths, Stoneham, Mass.; R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) Academic Press, San Diego, Calif.; I. Potrykus (1991) *Ann. Rev. Plant Physiol. Plant Mol. Biol.* 42:205; Weising et al. (1988) *Annu. Rev. Genet.* 22:421; van Wordragen et al. (1992) *Plant Mol. Biol. Rep.* 19:12; Davey et al. (1989) *Plant Mol. Biol.* 13:273; Walden and Schell (1990) *Eur. J Biochem.* 192:563; Joersbo and Brunstedt (1991) *Physiol. Plant.* 81:256 and references cited in those references. The references cited in the list of References attached below also provide a description of the terms used herein. The following U.S. patents are incorporated herein by reference: U.S. Pat. Nos. 5,959,180, 6,084,156, 6,940, 003, and 5,231,020. All references cited in the present application are expressly incorporated by reference herein.

To facilitate understanding of the invention, a number of terms are defined below.

The polypeptide encoded by the Stg3 gene is the enzyme UDP-glucose:solanidine glucosyltransferase, denoted herein as SGT2. As shown in FIG. 1, this enzyme catalyzes the first step in the synthesis of α-chaconine from solanidine.

As defined herein, "SGT2" includes all enzymes that are capable of catalyzing the UDP-glucose dependent conversion of solanidine to γ-chaconine. The amino acid sequence of the enzyme may or may not be identical with the amino acid sequence that occurs naturally in Solanaceous plants. In addition, artificially induced mutations are also included so long as they do not destroy activity. The definition of SGT2 used herein includes these variants that are derived by direct or indirect manipulation of the disclosed sequences.

It is also understood that the primary structure may be altered by post-translational processing or by subsequent chemical manipulation to result in a derivatized protein which contains, for example, glycosylated residues, oxidized forms of, for example, cysteine or proline, conjugation to additional moieties, such as carriers, solid supports, and the like. These alterations do not remove the protein from the definition of SGT2 so long as its capacity to catalyze the UDP-glucose dependent conversion of solanidine to γ-chaconine is maintained.

The identity of an enzyme as "SGT2" can be confirmed by its UDP-glucose-dependent ability to glucosylate solanidine in vitro.

Also, the identity of an enzyme as "SGT2" can be confirmed by its ability to reduce the accumulation of α-chaconine and or increase the accumulation of α-solanine when introduced in an antisense construct into potatoes.

While alternative forms of assessment of SGT can be devised, and variations on the above protocol are certainly permissible, the foregoing provides a definite criterion for the presence of SGT2 activity and classification of a test protein as SGT2.

Preferred forms of SGT2 of the invention include those illustrated herein and those derivable by systematic mutation of the genes. Such systematic mutation may be desirable to enhance the SGT2 properties of the enzyme, to enhance the characteristics of the enzyme which are ancillary to its activity, such as stability, or shelf life, or may be desirable to provide inactive forms useful in the control of SGT2 activity in vivo, as further described below.

The UDP-glucose:solanidine glucosyltransferase gene, denoted herein as SGT2, can also be described as SOLtu:SGT2.1 or SOLtu:SGT2.2, a member of the *Solanum tuberosum* sterolalkaloid glycosyl transferase gene family encoding the SGT2 enzyme, UDP-glucose:solanidine glucosyltransferase. The coding sequences are shown in SEQ ID NO:1 from nucleotide 7 to 1521 and in SEQ ID NO:3 from 1 to 1449.

Sgt2 coding sequences include all sequences in purified and isolated form that encode a polypeptide having SGT2 activity as defined above. The term "coding sequence" is defined herein as a nucleic acid sequence that directly specifies the amino acid sequence of its protein product, e.g., a sequence that is transcribed into MRNA and translated into a polypeptide. The boundaries of the coding sequence are generally determined by the ATG start codon (eukaryotes) and a translation terminator (stop codon). A coding sequence can include, but is not limited to, DNA, cDNA, and recombinant nucleic acid sequences.

Nucleic acid sequences having at least 99% sequence identity with SEQ ID NO:1 from nucleotide 7 to nucleotide 1521 or SEQ ID NO:2 from nucleotide 1 to nucleotide 1449 and having SGT2 activity are also encompassed by the present invention.

The term "identity," as known in the art, is a relationship between two or more polypeptide sequences or two or more polynucleotide sequences, as determined by a comparison of the sequences. In the art, "identity" also means the degree of sequence relatedness between polypeptide or polynucleotide sequences, as determined by the match between strings of such sequences. "Identity" can be readily calculated by known methods, including but not limited to those described in *Biocomputing: Informatics and Genome Projects*, Smith, D. W., ed., Academic Press, N.Y., 1993; *Computer Analysis of Sequence Data, Part I*, Griffin, A. M., and Griffin, H. G., eds., Humana Press, N.J., 1994; and *Sequence Analysis in Molecular Biology*, von Heinje, G., Academic Press, 1987. Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12 (1): 387 (1984)), BLASTP, BLASTN, and FASTA (Altschul, S. F. et al., *J. Molec. Biol.* 215: 403-410 (1990). The BLAST X program is publicly available from NCBI and other sources (BLAST Manual, Altschul, S., et al., NCBI NLM NIH Bethesda, Md. 20894; Altschul, S., et al., *J. Mol. Biol.* 215: 403-410 (1990) and Altschul et al., Gapped BLAST and PSI-BLAST: a new generation of protein database search programs. *Nucleic Acids Res.* 25:3389-3402 (1997).), ALIGN and ClustalW [Higgens, D. G. et al, 1989, *Comput. Appl. Biosci,* 5 (2), 151-3].

"Percentage of sequence identity" is determined by comparing two optimally aligned sequences over a comparison window, wherein the portion of the polynucleotide sequence or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. It is preferred that the comparison window is at least 50% of the coding sequence, preferably 60%, more preferably 75% or 85%, and even more preferably 95% to 100%.

Nucleic acid sequences which hybridize specifically to the Sgt2 coding sequence or its complement under high stringency conditions and which encode a polypeptide having SGT2 activity are also encompassed by the present invention. These include DNA sequences that hybridize specifically to an Sgt2 coding sequence or its complement.

The term "hybridization" as used herein includes "any process by which a strand of nucleic acid joins with a complementary strand through base pairing." [Coombs J (1994) *Dictionary of Biotechnology*, Stockton Press, New York N.Y.]. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

The phrase "hybridizes under stringent conditions" refers to the formation of a double-stranded duplex from two single-stranded nucleic acids. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid.

Nucleic acid probes to identify and clone DNA encoding polypeptides having the desired enzyme activity from strains of different genera or species can be prepared according to methods well known in the art. Such probes can be used for hybridization with the genomic or cDNA of the genus or species of interest, following standard Southern blotting procedures, in order to identify and isolate the corresponding gene therein. Both DNA and RNA probes can be used. The probes are typically labeled for detecting the corresponding gene (for example, with $^{32}P$, $^{3}H$, $^{35}S$, biotin, or avidin).

For purposes of this invention, it is preferred that probe hybridization of long probes of at least 100 nucleotides in length occurs under high stringency conditions. High stringency conditions when used in reference to nucleic acid hybridization comprise conditions equivalent to binding or hybridization at 68° C. in a solution consisting of 5X SSPE, 1% SDS, 5X Denhardt's reagent and 100 µg/ml denatured salmon sperm DNA followed by washing in a solution comprising 0.1X SSPE, and 0.1% SDS at 68° C. when a probe of about 100 to about 1000 nucleotides in length is employed, or the above-mentioned conditions with 50% formamide at 42° C. High stringency washes can include 0.1 X SSC to 0.2 X SSC, 1% SDS, 65° C., 15-20 min. An example of stringent wash conditions for a Southern blot of such nucleic acids is a 0.2 X SSC wash at 65° C. for 15 minutes (see, Sambrook et al., *Molecular Cloning—A Laboratory Manual* (2$^{nd}$ ed.) Vol. 1-3, Cold Spring Harbor Laboratory, Cold Spring Harbor Press, N.Y., 1989, for a description of SSC buffer). Other exemplary high stringency hybridization conditions include, for example, 7% SDS, 0.25 M sodium phosphate buffer, pH 7.0-7.2, 0.25 M sodium chloride at 65° C.-68° C. or the above-mentioned conditions with 50% formamide at 42° C.

For short probes which are about 15 nucleotides to about 70 nucleotides in length, stringency conditions are defined as prehybridization, hybridization, and washing post-hybridization at about 5° C. about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1X Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the material with immobilized DNA is washed once in 6X SCC plus 0.1% SDS for 15 minutes and twice each for 15 minutes using 6X SSC at 5° C. about 10° C. below the calculated $T_m$.

A genomic DNA or cDNA library prepared from other organisms may be screened for DNA that hybridizes with the probes described above and which encodes a polypeptide having the desired enzyme activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable material. In order to identify a clone or DNA that is homologous with a selected sequence or a subsequence thereof, the material with immobilized DNA is used in a Southern blot. For purposes of the present invention, hybridization indicates that the nucleic acid sequence hybridizes to a labeled nucleic acid probe corresponding to the selected nucleic acid sequence, its complementary strand, or a subsequence thereof, under high stringency conditions. Molecules to which the nucleic acid probe hybridizes under these conditions are detected using X-ray film.

The RNA equivalents of the Sgt2 sequences are encompassed by the present invention.

Gene Silencing/Antisense constructs: Use of sequences and/or constructs in gene silencing or antisense uses are encompassed by the present invention. Without being bound by theory, it is submitted that the sequences having Sgt2 activity, when used in gene silencing or antisense techniques, inhibit, decrease and/or prevent production of the SGT2 polypeptide and thereby reduce or eliminate SGT2 enzyme activity and reduce or eliminate accumulation of the steroidal glycoalkaloid end product α-chaconine and/or increase the accumulation of the steroidal glycoalkaloid end-product α-solanine as shown in FIG. 1. This is based on the chemical analysis of product accumulation. In this case, the end product α-chaconine is reduced, and/or the end product α-solanine is increased. The identity of the position of SGT2 as the solanidine glucosyltransferase in the biosynthetic pathway is confirmed by the demonstration of UDP-glucose dependent glucosylation of solanidine using purified recombinant SGT2 protein in in vitro biochemical assays.

Down-regulation of expression of an Sgt2 gene may be achieved using anti-sense technology or "sense regulation" ("co-suppression"). In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496. An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence. The sequence employed may be 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than 500 nucleotides may be used.

"Over expression" in the context of the invention refers to the production of the SGT2 gene product in transgenic organisms that exceeds levels of production in normal or non-transformed organisms. Over expression of the SGT2 enzyme of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same or different genes and also one or more introns in order to facilitate gene expression. 3' non-coding sequences encoding transcription termination signals may also be provided.

Crops in the *Solanaceae* family include potato (*Solanum tuberosum*); tomato (*Lysopersicon*, e.g., *L. lycopersicum* and *L. esculentum*); pepper (*Capsicum*); eggplant (*Solanum melongena*).

DETAILED DESCRIPTION OF THE INVENTION

The present invention is directed to the steroidal alkaloid glycosyl transferase enzyme UDP-glucose:solanidine glucosyltransferase (SGT2) that is involved in the biosynthesis of steroidal glycoalkaloids in Solanaceous plants. As discussed above, in cultivated potato the predominant glycoalkaloid species, α-chaconine and α-solanine, are triglycosylated derivatives of the aglycone solanidine. The first step in the synthesis of α-chaconine from the steroidal alkaloid aglycone solanidine is catalyzed by SGT2.

In particular, the invention is directed to an isolated nucleic acid molecule encoding a SGT2 polypeptide selected from the group consisting of:
  (a) a nucleic acid molecule with polypeptide coding sequence having at least 99% nucleotide sequence identity with SEQ ID NO:1 from nucleotide 7 to nucleotide 1521, with SEQ ID NO:3 or with SEQ ID NO:5 from nucleotide 19 to nucleotide 1011;
  (b) a nucleic acid sequence which encodes a polypeptide having at least 99% identity with SEQ ID NO:2 or SEQ ID NO:4;
  (c) a nucleic acid sequence which hybridizes under high stringency conditions with SEQ ID NO:1 from nucleotide 7 to nucleotide 1521, with SEQ ID NO:3 or with SEQ ID NO:5 from nucleotide 19 to nucleotide 1011;
  (d) a nucleic acid molecule as shown in SEQ ID NO:1, SEQ ID NO:3, SEQ ID NO:5, SEQ ID NO:14 or SEQ ID NO:16;
  (e) an RNA equivalent of the sequences of (a), (b), (c), or (d); and
  (f) a complement of the molecule defined in (a), (b), (c), (d) or (e).

A specific embodiment of an Sgt2.1 nucleotide sequence is given in SEQ ID NO:1. This DNA sequence is 1671 bp in length. The open reading frame (coding portion), initiating at base 7 and terminating at base 1521 encodes a protein 505 amino acids in length (SEQ ID NO:2). The novel gene SOLtu:Sgt2.1 was obtained from the source organism *Solanum tuberosum*.

Further, nucleic acid sequences which hybridize under high stringency conditions, as defined above, with the coding region of the DNA sequence of SEQ ID NO:1 or SEQ ID NO:3 and which encode a polypeptide which encode an SGT2 polypeptide are included in the present invention.

The invention further encompasses a complementary strand of a nucleic acid sequence or RNA equivalent of the above sequences.

The present invention is also directed to recombinant host cells, comprising a nucleic acid sequence for recombinant production of the polypeptides or for gene silencing as described above. Preparation of transformed host cells and cloning methods are described by U.S. Pat. No. 5,374,540, which is incorporated herein by reference. Plants or seeds transformed with one or more of the sequences is encompassed by the invention. The transgenic plant may be constructed in accordance with methods known in the art. A specific example is set forth below.

A particular use of the nucleic acid sequences, portion thereof, complement or RNA equivalent is to inhibit SGT2 activity and reduce the levels of the steroidal glycoalkaloids α-chaconine and/or increase the levels of the steroidal glycoalkaloid α-solanine in Solanaceous plants. SEQ ID NO:5 shows an Sgt2 partial sequence that was used for construction of antisense constructs for the transgenic plant lines. This is described in detail in the Example below.

The present invention is also directed to isolated polypeptides having SGT2 activity, selected from the group consisting of:
  (a) a polypeptide having at least 99% sequence identity with SEQ ID NO:2, SEQ ID NO:4, SEQ ID NO:15, or SEQ ID NO:17;
  (b) a polypeptide encoded by a nucleic acid molecule with polypeptide coding sequence having at least 99% nucleotide sequence identity with SEQ ID NO: 1 from nucleotide 7 to nucleotide 1521, with SEQ ID NO:3 or with SEQ ID NO:5 from nucleotide 19 to nucleotide 1011;
  (c) a polypeptide encoded by a nucleic acid sequence which hybridizes under high stringency conditions with SEQ ID NO:1 from nucleotide 7 to nucleotide 1521, with SEQ ID NO:3 or with SEQ ID NO:5 from nucleotide 19 to nucleotide 1011;
  (d) a polypeptide having the amino acid sequence of SEQ ID NO:2, SEQ ID NO:4, SEQ ID NO:15, or SEQ ID NO:17.

METHODS OF USE

The invention encompasses methods of use of the sequences and enzyme. A particular use of the nucleic acid sequences and portions thereof is to inhibit SGT2 activity and reduce the levels of the steroidal glycoalkaloid α-chaconine and/or increase levels of the steroidal glycoalkaloid α-solanine in Solanaceous plants. Another use of the nucleic acid sequences of the invention is to express SGT2 protein in bacteria or yeast by placing the full-length SGT coding sequence under control of a suitable promoter and terminator. The promoter can be constitutive or inducible, depending upon the potential toxicity of the expressed protein. The protein can be expressed in its native configuration—unmodified, or can be fused to an antibody epitope or metal affinity tag to facilitate purification and in vitro biochemical analysis. Other uses of the sequences of the invention are to express or over express the SGT2 enzyme in a transgenic plant. The sequences of the invention can also be used as probes capable of detecting the SGT2 gene or fragment thereof, and in methods to obtain purified SGT2.

EXAMPLE

The following example is intended only to further illustrate the invention and is not intended to limit the scope of the invention that is defined by the claims.

MATERIALS AND METHODS

Plant Material

Potato (*Solanum tuberosum L.*) cv. Lenape [Akeley, et al., (1968) American Potato Journal, 45:142-151] was grown in a glass-house in Albany, Calif. for collection of meristems for DNA isolation. For SGA and MRNA analyses, Lenape tubers were harvested from field plots [Coetzer, et al., (2001) *J. Agric. Food Chem.*, 49:652-657) in Aberdeen, Id. USA and Desirée tubers were harvested from glasshouse-grown plants in Invergowrie, Dundee, UK.

To examine wound responses tuber and leaf material was collected from glass house grown plants. Tubers were sliced into 2 mm slices and incubated in the dark for the times indicated. Fully expanded leaves were excised, clamped over 50% of the leaf surface with a hemostat, and incubated in the dark for the times indicated.

cDNA Sequences

Identification of a putative SGT2 coding sequence was accomplished by screening the TIGR expressed sequence tag (EST) database of expressed potato genes. The EST database was searched for sequences whose predicted protein translation contained homology to the known SGT1 [Moehs, et al., (1997) *Plant J.*, 11:227-236) (GenBank Accession no. U82367). The candidate TC sequence was then checked for the frequency of occurrence and tissue distribution of the component ESTs as compared to Sgt1. The most homologous sequence was TC10074 (1,178 bp). Sgt2 cDNA sequences were amplified by PCR from a wound-induced tuber cDNA library prepared from *S. tuberosum* cv. Lemhi [Garbarino, et al., (1992) *Plant Mol. Biol.*, 20:235-244). Internal primers [Forward: #1384 CTTCCT-TCCTTACTTCGCC (SEQ ID NO:6); and #1386 GGATAACGGGAGCAAGC (SEQ ID NO:7); and Reverse: #1414 GATGGTTAGTTGCGGTGC (SEQ ID NO:8)] were used for the amplification of Sgt2 sequences of 1,036 and 1,066 bp, respectively. An additional outward facing primer was matched with M13 vector primers to obtain Sgt2 cDNA 3-prime terminal regions [#1453 TACCGTC-CCTTTCATTTGG (SEQ ID NO:6)] for cloning into pCR2.1 (TA cloning vector, Invitrogen).

For expression of SGT2 protein in yeast, additional full length SGT2 coding sequences were amplified by PCR directly from the *S. tuberosum* cv. Lemhi cDNA library [Garbarino, et al., (1992) *Plant Mol. Biol.*, 20:235-244). Amplification was performed with primers directed to the 5-prime and 3-prime ends of the longest open reading frame (ORF) in Sgt2 [Forward: #1618 GGTACCATG-GATAACGGGAGCAAGCC (SEQ ID NO:11), and Reverse: #1619 GGTACCGTTGTTAATCCATGATCT-TCAATG (SEQ ID NO:12), or #1623 CTCGAGATCCAT-GATCTTCAATGAAGAAG (SEQ ID NO:13)]. The amplified fragments were cloned into the pYES 2.1 V5/TOPO expression vector (Invitrogen). A KpnI site addition to the Met start codon provides an optimal Kozak start consensus for the recombinant protein (#1618) (SEQ ID NO:14). An XhoI replacement of the native stop (#1623) (SEQ ID NO:16) gives the construct a read-through fusion to the V5 antibody epitope and 6xHis C-terminal tag in the pYES2.1/V5-His TOPO cloning vector (Invitrogen). Yeast was transformed with the recombinant vectors and grown under inducing conditions. Protein was extracted according to manufacturer's recommendations (Invitrogen).

Protein purification and analysis

Protein purification (SEQ ID NO:17) was carried out using the His protein isolation system (Sigma) according to manufacturer's instructions. Purification was assessed via SDS PAGE and staining with Coomassie blue. Elution of recombinant proteins was monitored by Western blot analysis using the anti-V5 epitope antibody (Invitrogen). Solanidine glycosyltransferase assays were carried out using 100 µL of column eluate after buffer exchange and concentration. Assays were run for 60 minutes at 37° C. SGAs and UDP-sugars were provided at 33 µM unless otherwise indicated. Radioactive UDP-sugar stock solutions were prepared to contain ~5×10$^5$ dpm UDP-[$^3$H]glucose or UDP-[$^3$H]galactose per reaction. Inhibitor studies included the addition of α-solanine or α-chaconine dissolved in DMSO to the final concentrations as indicated. Control reactions had the addition of an equal volume of DMSO in the absence of inhibitor. Products were separated using anion exchange resin [Stapleton, et al., (1991) *J. Agric. Food. Chem.*, 39:1187-1193). No activity is reported for reactions with less than 2-fold the average dpm counts of the blank reactions. Values are the mean of duplicate assays.

Antisense Transgene Construction

The antisense transgene was constructed with a 1,011 bp HincII/EcoRV sub-fragment of the Sgt2 amino terminal fragment including 18 bp of vector on the EcoRV end (SEQ ID NO:5). The fragment was ligated in antisense orientation downstream of a 1,206 bp potato GBSS6 promoter [van der Liej, et al., (1991) *Mol Gen Genet*, 228:240-248), for tuber-specific transcription [van der Steege, et al., (1992) *Plant Mol Biol*, 20:19-30), followed by a 404 bp potato Ubi3 polyadenylation signal [Garbarino and Belknap, (1994) *Plant Mol Biol*, 24:119-127). The transgene is inserted in a modified pBINPLUS binary vector [van Engelen, et al., (1995) *Transgenic Research*, 4:288-290), pBINPLUS/ARS, for mobilization into potato varieties Lenape and Desirée via Agrobacterium-mediated transformation [Snyder and Belknap, (1993) *Plant Cell Reports*, 12:324-327). The pBINPLUS/ARS vector is identical to pBINPLUS except that control sequences for the NptII plant selectable marker (nopaline synthase promoter and terminator pBINPLUS) have been replaced by potato Ubi3 promoter and polyadenylation signal [Garbarino and Belknap, (1994) *Plant Mol Biol*, 24:119-127) sequences in pBINPLUS/ARS.

Plant Transformation with Antisense Transgene Construct

The antisense transgene construct was mobilized into potato varieties Lenape [Akeley, et al., (1968) *American Potato Journal*, 45:142-151) and Desirée via Agrobacterium-mediated transformation [Snyder and Belknap, (1993) *Plant Cell Reports*, 12:324-327).

Steroidal Glycoalkaloid Determinations

Levels of SGAs were quantified from field-grown Lenape or glasshouse-grown Desirée. Freeze dried material was produced from Lenape and Desirée tubers as described by McCue et al. (2005) and Defernez et al. (2004).

Glycoalkaloid levels were determined by an LC-MS method on a Thermo LCQ-DECA (Hemel Hempstead, UK) LC-MS. Glycoalkaloids were separated on a $C_{18}$ Synergi Hydro column (2 mm×150 mm; Phenomenex, Macclesfield, UK). Chromatographic conditions were as follows; Flow rate, 200 µl min.$^{-1}$; 1 min. at 0.2% $HCO_2H$ in $dH_2O$ then a linear gradient to 0.2% $HCO_2H$ in $CH_3CN$-$dH_2O$ (9:1) over 20 min., followed by re-equilibration at 0.2% $HCO_2H$ in $dH_2O$ for 5 min.

Glycoalkaloid analyses employed electrospray ionization-mass spectrometry (ESI-MS) with the following MS conditions; sheath gas (N2) 70 psi, auxiliary gas 15 psi, spray voltage 4500 V and capillary temp. 250° C. α-Solanine and α-chaconine were quantified using calibration curves constructed within the analytical run and employed the following ions specific for calibration and estimation; α-solanine—m/z 868.8 [M+H]+ and a-chaconine —m/z 852.7 [M+H]+. Five calibration points were repeated four times, as were the tuber analyses. Statistical analysis of data was performed by One Way ANOVA (SigmaStat 3.1 for Windows 2004. Systat Software, Inc.) for triplicate Lenape data and by Dunnett's test (SAS Institute Inc. 2004. SAS OnlineDoc™ 9.1.3. Cary, N.C.: SAS Institute Inc.) for duplicate Desirée data, using unequal variances (Littell, et al., 2002).

RNA Blots

Total RNA was prepared from tuber peels obtained using a hand-held vegetable peeler. Peels were frozen in liquid nitrogen, ground and extracted for RNA as previously described [Verwoerd, et al., (1989) *Nucleic Acids Res.*, 17:2362). RNA was isolated and fractionated by agarose gel electrophoresis, and transferred to a charged nylon membrane (Roche) [Rickey and Belknap, (1991) *Plant Mol. Biol.*, 16:1009-1018). RNA blots were hybridized with random primed (GE Healthcare) double stranded probes of the: Sgt1 cDNA (1,582 bp) [Moehs, et al., (1997) *Plant J.*, 11:227-236), Sgt2 cDNA (1,066 bp), or the NptII (803 bp) selectable marker isolated with a PmeI digest of pBINPLUS/ARS.

DNA Blots

DNA was isolated from young shoot tips frozen in liquid nitrogen and extracted as previously described [Draper and Scott, (1988) Plant Genetic Transformation and Gene Expression: A Laboratory Manual:199-236). DNA was digested with restriction enzymes as indicated in the figure legends, separated by agarose electrophoresis, blotted to charged nylon membranes, and hybridized with the double stranded Sgt2 fragment (1,066 bp) or the NptII (803 bp) selectable marker isolated with a PmeI digest of pBINPLUS/ARS.

RESULTS

SGT2 sequence identity and protein homology

The Sgt2 sequence was identified in the TIGR EST database searching for protein homology with the deduced SGT1 sequence. Nine Sgt2 cDNA fragments of 1,036 or 1,066 bp of the amino-terminal coding region were isolated using PCR with synthetic oligos. An antisense vector was constructed from the longer fragment and was used to transform potatoes. cDNAs for the carboxyl-terminal coding region and UTR were obtained in separate rounds of PCR. Eight clones with unique length poly(A) tails were obtained. Two ESTs with 3' UTRs of different lengths are present in the TIGR database; indicating multiple polyadenylation sites. No clones containing 5-prime upstream UTR sequences for Sgt2 longer than the existing ESTs in the TIGR database were obtained from the cDNA library.

The composite cDNA containing the entire coding sequence was designated SOLtu:Sgt2.1 (Sgt2, GenBank Accession no. DQ218276). It was 1,659 bp in length (SEQ ID NO:1) and contained an open reading frame encoding a 489 residue polypeptide (SEQ ID NO:2). The consensus Sgt2 cDNA isolated from *S. tuberosum* cv. Lemhi showed a 99% identity to the Sgt2 tentative consensus (TC) assemblage in the TIGR database. Comparing the coding region of Sgt2 to that of Sgt1, the previously identified potato sterol alkaloid galactosyltransferase, revealed a 64% nucleic acid identity (FIG. 2). This suggests that an antisense approach to silence one gene would not affect the other. Protein alignment of SGT2 to SGT1 showed an overall 73% conservation-and 63% amino acid identity (FIG. 3). SGT2 also exhibited high identity and homology to other glycosyltransferases in several regions including the putative substrate binding recognition portion (amino acids #s 107-149), and the UDP-sugar binding region (amino acid #s 348-403), including the potential active site histidine residues (#360, #369) [Nawloka, et al., (2003) *Acta Biochim. Pol.*, 50:567-572).

Occurrence of the SGT2 locus in *S. tuberosum*

Figure 4:
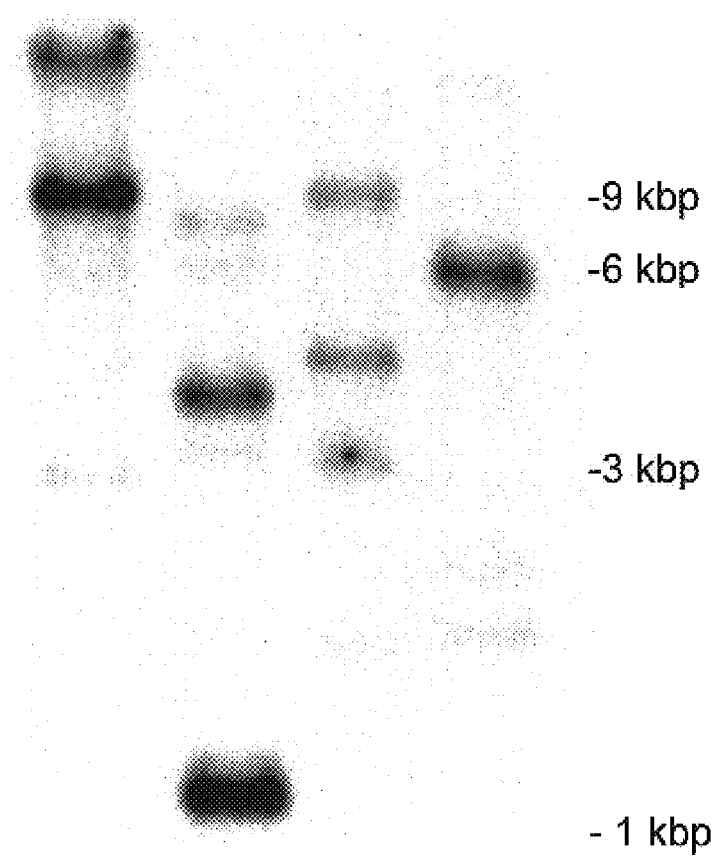
FIG. 4 shows the occurrence of Sgt2 in the potato genome. Genomic analysis using 10 μg DNA from *S. tuberosum* cv. Lenape cut with the restriction endonucleases as indicated and probed with the 1,066 bp amino terminal fragment of Sgt2. Sgt2 is a low copy gene in the potato genome with 2 to 4 copies likely representative of a single allele on each of the chromosome homologs and homoeologues.

The approximate copy number and allelic variation of Sgt2 in *S. tuberosum* was evaluated using genomic DNA blot analysis. FIG. 4 shows the banding patterns after digestion with 4 different restriction endonucleases. BamHI was not predicted to cut within the Sgt2 cDNA whereas EcoRI, HinDIII and XbaI were all predicted to cut once within the coding region towards the 3-prime end of the probe. This favors stronger hybridization to the 5-prime half of the gene. Each digest resulted in 1-2 strong bands and 2-4 lighter bands. Digests with more than 2 lighter bands may represent restriction polymorphisms distal to the 3-prime end in some of the alleles. BamHI was not predicted to cut the Sgt2 cDNA sequence, yet two weak bands are present, so two or more weakly hybridizing bands may represent truncated pseudogenes, unknown introns or unrelated sequences. The relatively small number of bands, and expected presence of up to four alleles in tetraploid *S. tuberosum* suggests that Sgt2 is present as a single copy per haploid genome.

Steroidal glycoalkaloid accumulation

Figure 5A:
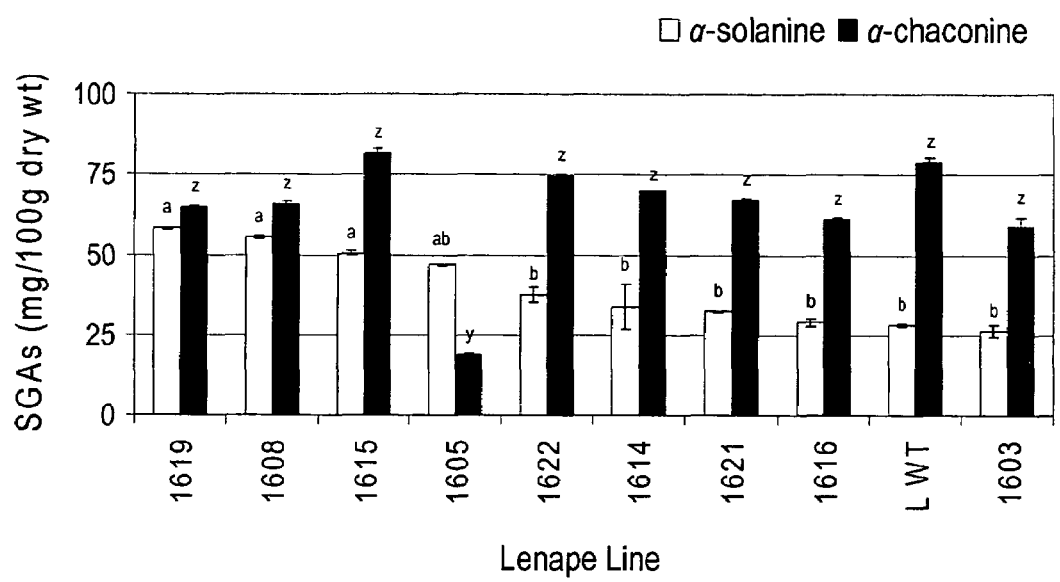
FIG. 5 shows SGA content of tubers from transgenic potatoes expressing the Sgt2 antisense transgene. Levels of α-solanine and α-chaconine in selected transgenic and wild type (WT) control lines of a) Lenape (FIG. 5A) and b) Desirée (FIG. 5B). The plant lines are arranged in the graphs sorted by decreasing α-solanine levels. Values are the average of 3 slices from 3 field-grown tubers (Lenape) or 2 glasshouse-grown minitubers (Desirée). Error bars show s.d., unique letters indicate statistical significance P>0.05.
Figure 5B:
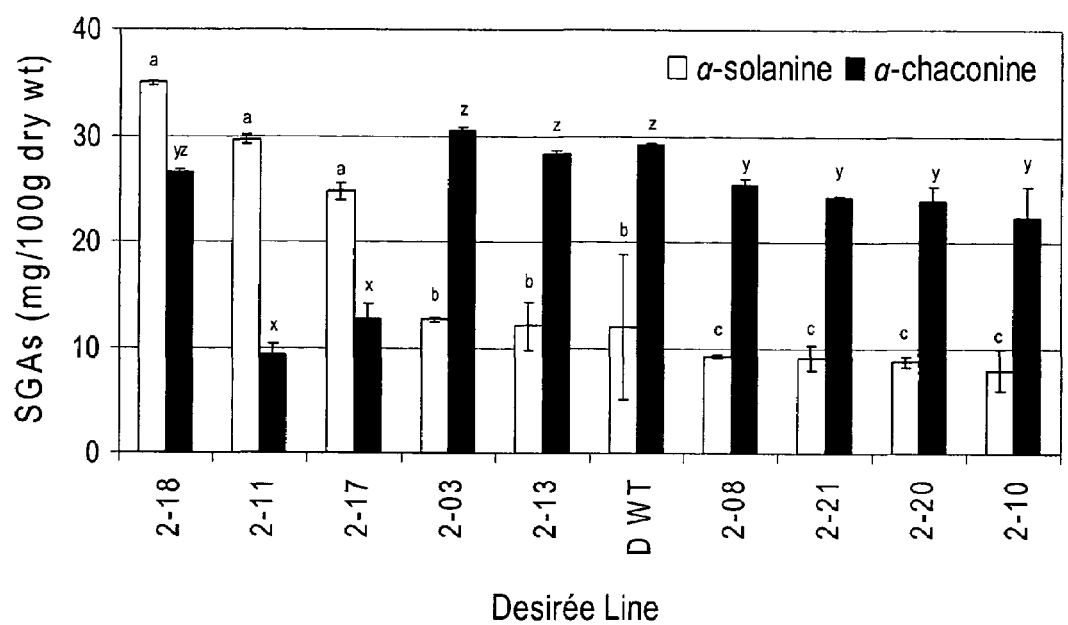

The SGA levels ($\alpha$-solanine and $\alpha$-chaconine) were measured in uniform slices of field-grown tubers of Lenape (FIG. 5A) or whole glasshouse-grown minitubers of Desirée (FIG. 5B). The range in total SGA levels ($\alpha$-solanine+$\alpha$-chaconine) for Lenape Sgt2 antisense lines varies from 23% above to 39% below the wild type control. Similar variation was observed in the Desirée Sgt2 antisense lines (50% above to 27% below). This variation has now been stable over three generations and is within the range attributable to somaclonal variation [Esposito, et al., (2002) *J Agric Food Chem*, 50:1553-1561). The variation in total SGA levels between lines and individual tubers makes it difficult to elucidate effects of antisense constructs on the accumulation of either $\alpha$-solanine or $\alpha$-chaconine. However, an examination of the ratio of $\alpha$-solanine to $\alpha$-chaconine quickly highlights the plants with an effective antisense response. In Lenape lines 1605, 1608 and 1619, and Desirée lines 2-11, 2-17 and 2-18, the ratio of $\alpha$-solanine to $\alpha$-chaconine was noticeably altered compared to wild type. In these lines effective antisense Sgt2 action modified the balance between glucosyl transferase and galactosyltransferase activity. In most of the affected lines $\alpha$-chaconine levels were reduced and there was increased $\alpha$-solanine accumulation. In lines 1608, 1619 and 2-18, the total SGA levels are increased (perhaps due to somaclonal variation), but the antisense Sgt2 activity affects the ratio of $\alpha$-solanine to $\alpha$-chaconine. The reductions in total SGAs and in $\alpha$-chaconine in Lenape line 1605 were both statistically significant ($P<0.001$), as was the reduction of $\alpha$-chaconine in Desirée lines 2-11 and 2-17 (both at $P<0.001$).

Analysis of transgene integration

Figure 6:
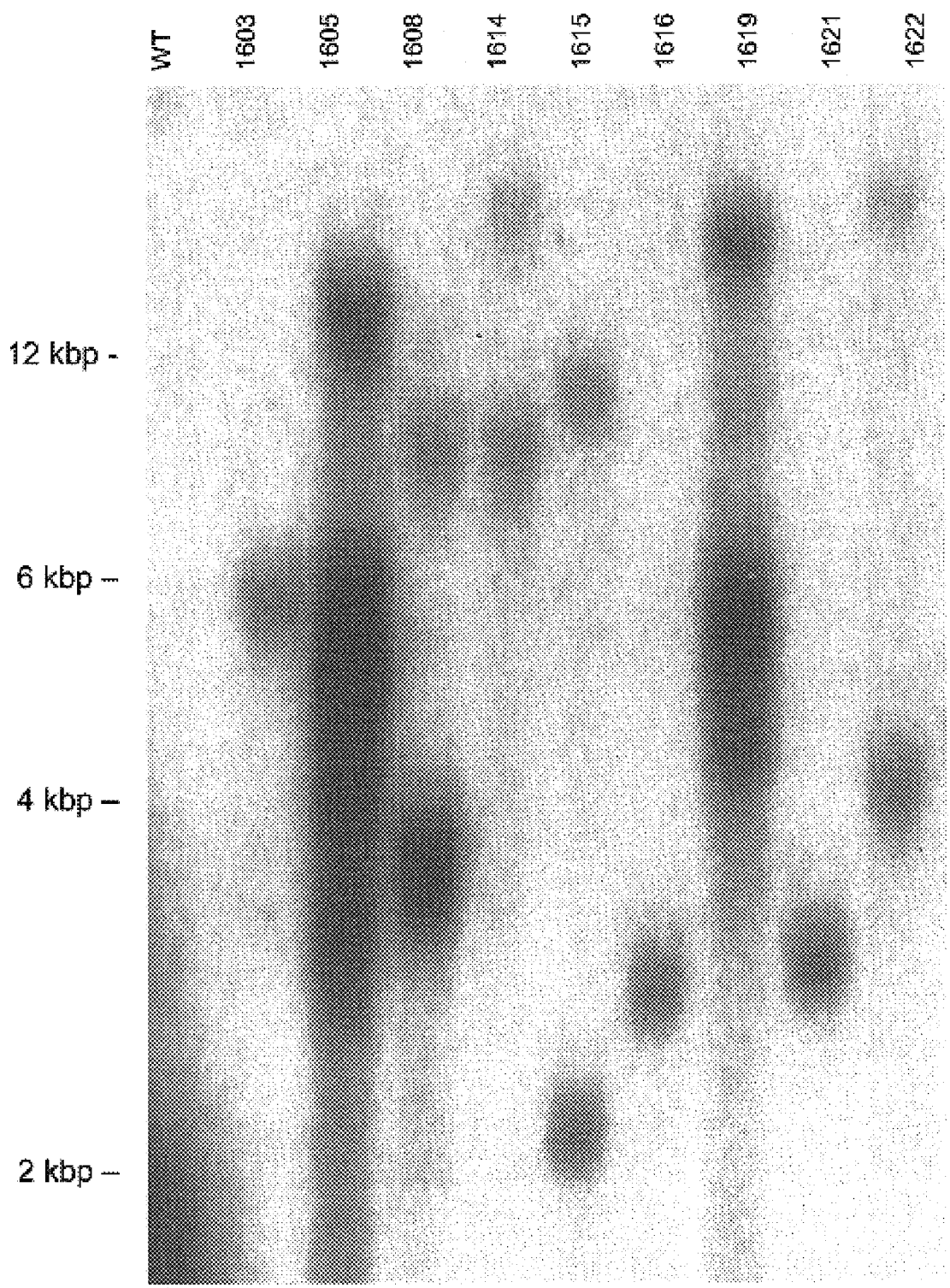
FIG. 6 shows integration patterns of antisense Sgt2 transgene in Lenape lines. Genomic DNA blot analysis of T-DNA insertion in control and transgenic lines of Lenape. Genomic DNA (20 μg/lane) was digested with HinDIII and probed with the complete NptII coding sequence.

To examine the affect of transgene integration on antisense transgene expression, genomic DNA was examined for integration patterns by DNA blot analysis. HinDIII digested DNA was probed with the NptII selectable marker gene to eliminate background bands due to the endogenous Sgt2 gene. HinDIII is predicted to cut once within the T-DNA construct and produce a fragment >1,723 bp. The result was a simple pattern of bands with single copy inserts in lines 1603, 1616 and 1621 and two copies in lines 1614, 1615, and 1622. In lines 1605, 1608 and 1619 however, very dark banding patterns were observed suggesting multiple insertions (FIG. 6).

Expression of antisense SGT2

Figure 7A:
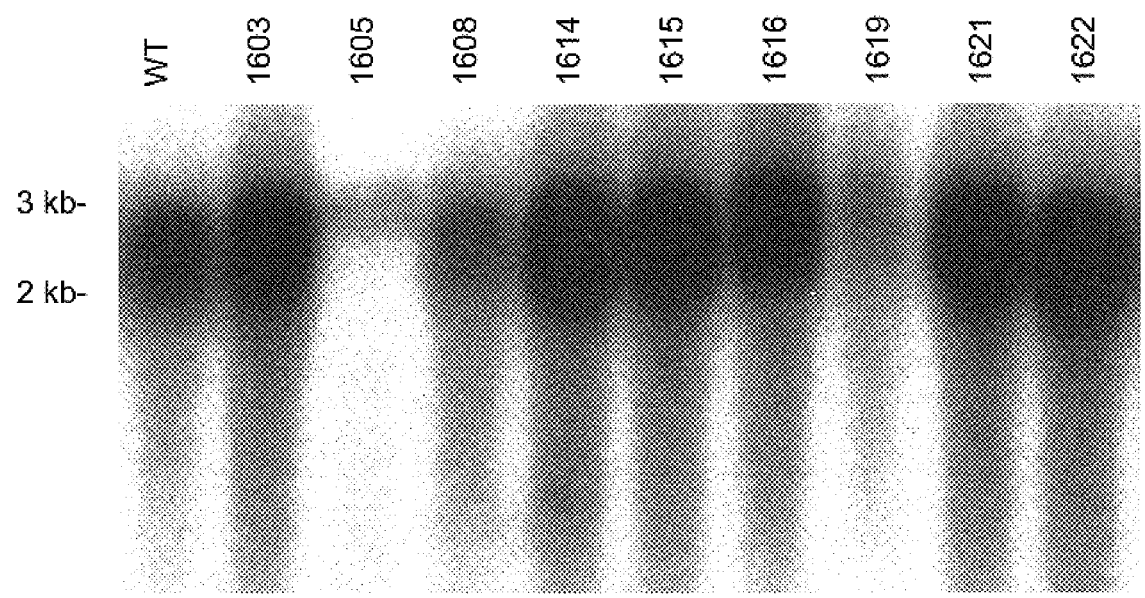
FIG. 7 shows analysis of total RNA (30 μg/lane) isolated from control and transgenic lines of Lenape. Analysis of: A) Sgt2 messenger levels, B) NptII messenger levels, and C) the ethidium bromide stained gel.
Figure 7B:
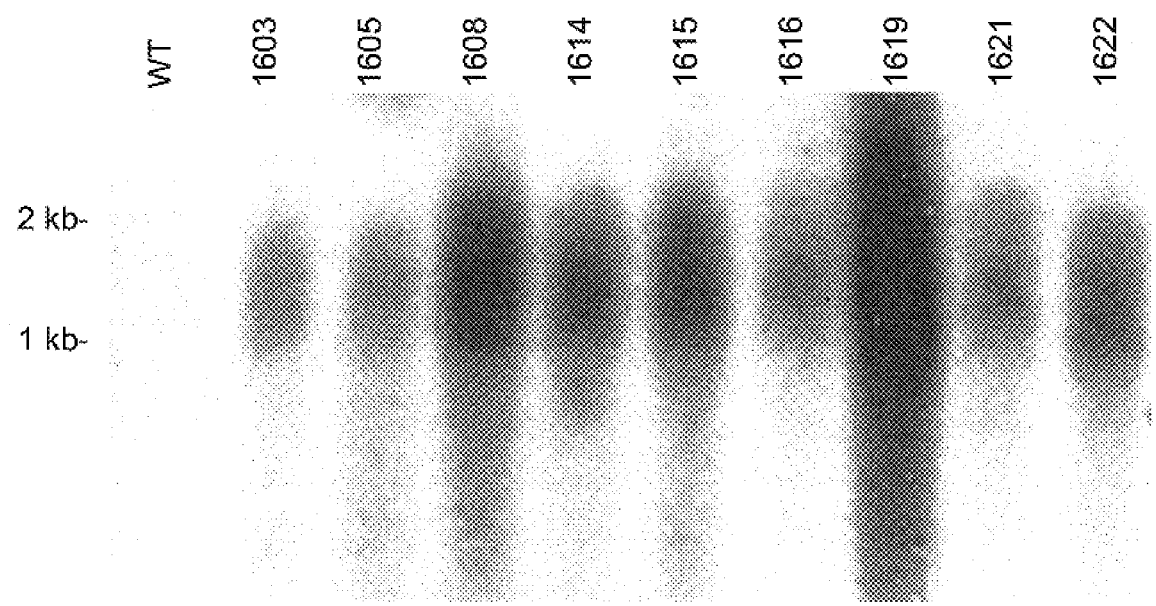
Figure 7C:
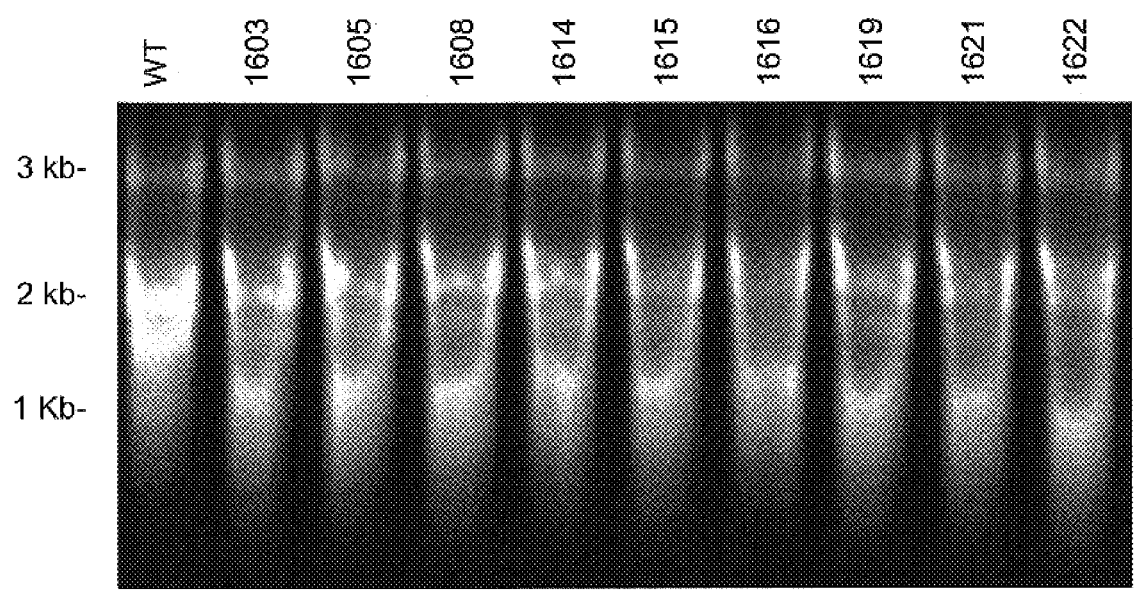

Steady state levels of Sgt2 mRNA were examined by RNA blot analysis. To test for transgene efficacy in down-regulating Sgt2 expression, RNA was isolated from transgenic tissue and was probed with the Sgt2 sequence (FIG. 7A). Reduced steady state levels of Sgt2 transcripts were observed in lines 1605 (almost completely lacking endogenous transcripts), 1608 and 1619, indicative of effective antisense transgenes where both sense and antisense message are degraded resulting in reduced activity of the SGT2 protein [Robert, et al., (1989) *Plant Mol Biol,* 13:399-409). The RNA blot was re-probed with the NptII selectable marker (FIG. 7B). This probe revealed strong bands in all lines with the exception of the control. The single copy insert lines resulted in the lowest levels of NptII mRNA abundance; two copy insert lines had higher levels, and the multiple copy insert lines had the highest levels. The exception was line 1605 with multiple copy inserts did not have high levels of NptII mRNA. This may be due to suppression of NptII along with Sgt2 or an absence of additional complete copies of NptII in the complex integration. The ethidium bromide stained gel was used to confirm RNA quality and loading consistency (FIG. 7C).

Isolation of Sgt2 coding sequences and expression vector construction

Recombinant SGT2 protein was prepared by expressing the intact coding sequence isolated from the wounded tuber cDNA library by PCR. The PCR resulted in 14 isolates identical to the original Sgt2 amino-terminal fragment and 5 isolates 99.7% identical with a 21 bp deletion (SOLtu: Sgt2.2, GenBank Accession no. DQ218277) (SEQ ID NO:3). A TC in the TIGR database that is distinct from the original Sgt2 and contains the same 21 bp deletion has since been generated. Extensive homology between the two alleles suggests that both alleles would be simultaneously down-regulated in plants expressing effective antisense genotypes. Both proteins were expressed and tested for glucosyltransferase activity in situ in yeast (data not shown). Only the more abundant SGT2 (based on our coding region amplification results and TIGR EST abundance) was purified and assayed in vitro.

Biochemical analysis of SGT2

The observation that the major effect of antisense Sgt2 was to reduce α-chaconine levels suggested that it served as the primary solanidine glucosyltransferase. This was confirmed by in vitro studies on the activity of recombinant SGT2 protein with Solanaceous SGAs and either UDP-[$^3$H] glucose or UDP-[$^3$H]galactose as the sugar donor (Table I). The recombinant SGT2 was readily capable of utilizing UDP-glucose as a substrate in vitro with all three *Solanaceous* aglycones (solanidine, solasodine and tomatidine) with maximum activity obtained with the potato aglycone solanidine. No activity was observed with UDP-galactose as a substrate for any of the aglycones tested. The threshold for activity was set at 2-fold the reaction blank.

Inhibition studies were performed using a separate SGT2 enzyme preparation (activity of 410 ±22 nkat mg$^{-1}$) (Table II). The addition of UDP-galactose had no competitive effect on SGT2 activity. This is contrary to a previous report that showed inhibition by UDP-galactose when a mixture of partially purified SGT2 was used in the presence of SGT1 (Bergenstråhle, et al., 1992). The addition of 1,000 µM α-solanine caused a 39% inhibition while, 1,000 µM α-chaconine completely inhibited SGT2 activity. This demonstrates weak feedback inhibition of the primary glucosylation step by both downstream triose end products.

CONCLUSIONS

The two Sgt2 sequences (Sgt2.1 and Sgt2.2) isolated from the *S. tuberosum* cDNA library likely represent two major alleles expressed in the heterozygous tetraploid genome. Subsequent to our isolation of these genes, the addition of more ESTs to the *Solanum tuberosum* Gene Index has resulted in the assembly of two independent TC sequences representing each allele. The presence of no more than two major bands in the genomic DNA blot analysis indicates that Sgt2 is a low copy gene in *S. tuberosum*. This in combination with two distinct coding sequences from PCR and in the EST database suggests that there are only two major active alleles.

The two solanidine glycosyltransferases represent the committed steps for carbon flow into the SGA pathway. Down-regulation of either Sgt1 or Sgt2 tends to cause an increase in the accumulation of the end product of the other branch, α-chaconine α-solanine, respectively. The reduction and compensation is greater in plant lines expressing effective antisense Sgt1 than in plant lines expressing effective antisense Sgt2. This may be due to the subtle differences in the substrate specificities for these two enzymes. SGT2 is very specific for UDP-glucose as a sugar donor completely lacking any galactosyltransferase activity. SGT1 has a marked preference for UDP-galactose, but does have some glucosyltransferase activity [Moehs, et al., (1997) *Plant J.,* 11:227-236; McCue, et al., (2005) *Plant Sci.,* 168:267-273), and may partially function in vivo in the absence of normal SGT2 activity.

The effective Lenape antisense lines show a consistent correlation with multiple T-DNA inserts, reduction in steady state levels of Sgt2 RNA, and either reduced α-chaconine and/or an increased α-solanine accumulation. All of this is consistent with the conclusion that SGT2 is the primary in vivo solanidine glucosyltransferase in a dedicated branch of SGA biosynthesis specific for the formation of α-chaconine. Based on these data we assign the function of the gene product SGT2 as E.C. 2.4.1.173, a UDP-glucose 3-β sterol glucosyltransferase.

Suppression of SGT2 in potato plants causes a reduction in α-chaconine levels and/or an increase in α-solanine levels. This results in a four-fold beneficial effect.

Figure 8:
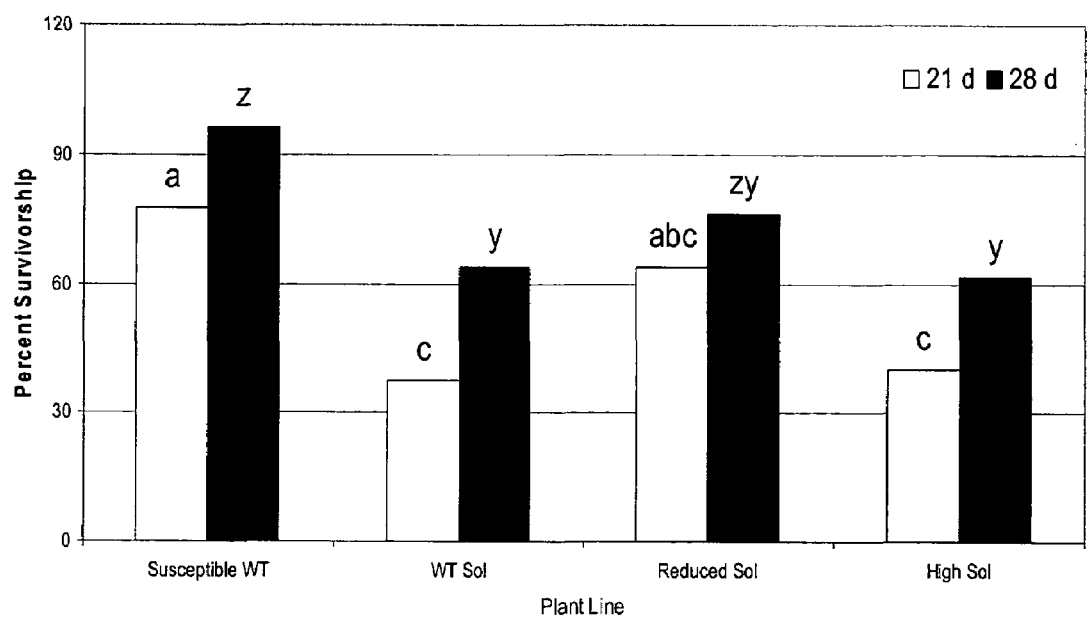
FIG. 8 shows the percent survival of Potato Tuber Moths feeding on tubers with different levels of α-chaconine and α-solanine. Moth larvae reared on tubers with reduced α-solanine correlated with larval survival indistinguishable from the susceptible control plant line. Moth larvae reared on tubers with normal or elevated levels of high levels of α-solanine had lower percent survival.

1. Reduction of SGT2 activity can reduce the accumulation of α-chaconine and reduce the overall levels of total steroidal glycoalkaloids allowing development of potato varieties with improved food safety.
2. Reduction of α-chaconine results in tubers with reduced human toxicity. α-chaconine is less toxic than its counterpart α-solanine. Even a shift in the ratio of α-solanine to α-chaconine in the absence of a reduction of total steroidal glycoalkaloids has a beneficial food safety effect.
3. Suppression of α-chaconine with the concomitant increase in α-solanine in the tubers will result in increased insect resistance. This inverse of this has been shown in our studies with Potato Tuber Moth larvae, that tubers with lowered α-solanine levels are more insect susceptible (FIG. 8).
4. Suppression of α-chaconine with the concomitant increase in α-solanine in the leaves will make potatoes more resistant to insect herbivores such as the Colorado potato beetle. Results from the literature demonstrate that α-solanine is more toxic to the Colorado potato beetle. This has been shown using artificial diets that higher alpha-solanine in leaves make them more resistant [Kowalski, et al., (1999) *Am. J. Potato Res.*, 76:305-312).

It is understood that the foregoing detailed description is given merely by way of illustration and that modification and variations may be made within, without departing from the spirit and scope of the invention. All publications, patents, published applications, and sequence listings cited herein are hereby incorporated by reference in their entirety.

---

The invention claimed is:

1. An isolated nucleic acid molecule encoding a SGT2 polypeptide having UDP-glucose:solanidine glucosyltransferase activity, wherein said nucleic acid molecule is selected from the group consisting of:
   (a) a nucleic acid molecule with polypeptide coding sequence having at least 99% nucleotide sequence identity with SEQ ID NO:1 [from nucleotide 7 to nucleotide 1521, with SEQ ID NO:3 or with SEQ ID NO:5 from nucleotide 19 to nucleotide 1011 ];
   (b) a nucleic acid sequence which encodes a polypeptide having at least 99% identity with SEQ ID NO:2 [or SEQ ID NO:4];
   (c) a nucleic acid sequence which hybridizes under high stringency conditions with SEQ ID NO:1 [from nucleotide 7 to nucleotide 1521, with SEQ ID NO:3 or with SEQ ID NO:5 from nucleotide 19 to nucleotide 1011], wherein said high stringency conditions comprise hybridization at 68° C. in a solution consisting of 5X SSPE, 1% SDS, 5X Denhardt's reagent and 100 µg/ml denatured salmon sperm DNA followed by washing in a solution comprising 0.1X SSPE, and 0.1% SDS at 68° C.;
   (d) a nucleic acid molecule as shown in SEQ ID NO:1 [, SEQ ID NO:3, SEQ ID NO:5, SEQ ID NO:14 or SEQ ID NO:16];
   (e) an RNA equivalent of the sequences of (a), (b), (c), or (d); and
   (f) a full-length complement of the molecule defined in (a), (b), (c), (d) or (e).

2. A nucleic acid construct comprising a nucleic acid molecule of claim 1 operably linked to one or more control sequences that direct the regulation of SGT2 polypeptide in an expression host.

3. A cell transformed with the isolated nucleic acid molecule of claim 1.

4. A plant transformed with the isolated nucleic acid molecule of claim 1.

5. A transgenic seed of the plant according to claim 4, wherein said seed contains said isolated nucleic acid molecule.

6. The plant of claim 4 wherein the plant is a Solanaceous plant.

7. The plant of claim 6 wherein the Solanaceous plant is potato.

8. Sexually or asexually obtained progeny of the plant of claim 4, wherein said progeny contains said isolated nucleic acid molecule.

9. A method of producing a SGT2 polypeptide having UDP-glucose:solanidine glucosyitransferase activity, which comprises cultivating a transformed host cell having the nucleic acid molecule of claim 1 under conditions suitable for production of the polypeptide; and recovering the polypeptide.

10. The method of claim 9, wherein said polypeptide is produced at a level exceeding that in a non-transformed cell.

11. The method of claim 9, wherein the SGT2 polypeptide having UDP-glucose:solanidine glucosyltransferase activity is a member selected from the group consisting of:
   (a) a polypeptide having at least 99% sequence identity with SEQ ID NO:2[, SEQ ID NO:4, SEQ ID NO:15, or SEQ ID NO:17];
   (b) a polypeptide encoded by a nucleic acid molecule with polypeptide coding sequence having at least 99% nucleotide sequence identity with SEQ ID NO:1 [from nucleotide 7 to nucleotide 1521, with SEQ ID NO:3 or with SEQ ID NO:5 from nucleotide 19 to nucleotide 1011];
   (c) a polypeptide encoded by a nucleic acid sequence which hybridizes under high stringency conditions with SEQ ID NO:1 [from nucleotide 7 to nucleotide 1521, with SEQ ID NO:3 or with SEQ ID NO:5 from nucleotide 19 to nucleotide 1011;], wherein said high stringency conditions comprise hybridization at 68° C. in a solution consisting of 5X SSPE, 1% SDS, 5X Denhardt's reagent and 100 µg/ml denatured salmon sperm DNA followed by washing in a solution comprising 0.1X SSPE, and 0.1% SDS at 68° C.; and
   (d) a polypeptide having the amino acid sequence of SEQ ID NO:2 [, SEQ ID NO:4, SEQ ID NO:15, or SEQ ID NO:17].

* * * * *